US005434247A

United States Patent [19]

[11] Patent Number: 5,434,247

[45] Date of Patent: Jul. 18, 1995

Jones

[54] PEPTIDES FOR INDUCING MONOCYTE CYTOTOXICITY IN DIAGNOSTICS

[75] Inventor: C. Michael Jones, Houston, Tex.

[73] Assignee: Board of Regents, The University of Texas System, Austin, Tex.

[21] Appl. No.: 901,717

[22] Filed: Jun. 17, 1992

Related U.S. Application Data

[60] Continuation-in-part of Ser. No. 624,053, Dec. 7, 1990, which is a division of Ser. No. 417,162, Oct. 4, 1989, Pat. No. 5,112,948, which is a continuation-in-part of Ser. No. 917,983, Oct. 10, 1986, Pat. No. 4,977,245.

[51] Int. Cl.[6] ........................ C07K 7/06; A61K 37/02

[52] U.S. Cl. .................................... 530/328; 530/329; 530/330; 530/331; 424/85.1

[58] Field of Search ............... 530/331, 330, 329, 328; 514/18, 12, 17, 16, 15; 424/85.1

[56] References Cited

U.S. PATENT DOCUMENTS

| | | | |
|---|---|---|---|
| 4,722,998 | 2/1988 | Cantor et al. | 530/351 |
| 4,785,077 | 11/1988 | Kornbluth et al. | 530/351 |
| 4,977,245 | 12/1990 | Jones | 530/35 |
| 5,112,948 | 5/1992 | Jones | 530/351 |

OTHER PUBLICATIONS

Yoshida, T. et al., "Migration Inhibitory Activity in Serum and Cell Supernatants in Patients with Sezary Syndrome," *The Journal of Immunology*, 114(3):915–918, 1975.

Broder, S. et al., "The Sézary Syndrome," *The Journal of Clinical Investigation*, 58:1297–1306, 1976.

Cohn, Zanvil A., "The Activation of Mononuclear Phagocytes: Fact, Fancy, and Future," *The Journal of Immunology*, 121(3):813–816, 1978.

Gmelig-Meyling, F., and Waldmann, T. A., "Separation of Human Blood Monocytes and Lymphocytes on a Continuous Percoll Gradient," *Journal of Immunological Methods*, 33:1–9, 1980.

Wiltrout, R. H. et al., "Indium-111 Assay of Macrophage-Mediated Cytolysis," *Manual of Macrophage Methodology; Collection, Characterization, and Function*, published by Marcel Dekker, Inc., pp. 337–344, 1981.

Okada, M. et al., "Establishment and Characterization of Human T Hybrid Cells Secreting Immunoregulatory Molecules," *Proceeding of the National Academy of Science, USA*, 78(12):7717–7721, 1981.

Fischer, D. G. et al., "Tumor Cell Killing by Freshly Isolated Peripheral Blood Monocytes," *Cellular Immunology*, 58:426–435, 1981.

Jones, C. M. et al., "Production of Both Macrophage Activating and Inhibiting Activities by a Murine T-Lymphocyte Hybridoma," *Nature*.

(List continued on next page.)

*Primary Examiner*—Robert J. Hill, Jr.
*Assistant Examiner*—Carol A. Salata
*Attorney, Agent, or Firm*—Arnold, White & Durkee

[57] ABSTRACT

The present disclosure relates to a new lymphokine molecule termed Monocyte Cytotoxicity Inducing Factor (MCF), to MCF peptides. The disclosure further relates to the development of novel Sezary cell hybridomas which secrete MCF, to the purification of MCF and its constituent polypeptides and to the identification of small peptides with MCF activity. Sezary OKT4+ lymphocytes were fused to CEM.8aza$^r$.C, an HGPRTase lacking clone of CEM, to generate hybrid cells, certain of which produced soluble mediators of human monocyte cytotoxicity. A single sezary hybrid clone, FtF3, produced a novel monocyte cytotoxicity inducing factor found to be distinct from IFN$\gamma$ and IFN$\alpha$. MCF, purified by dye ligand and ion-exchange chromatography, comprises two polypeptides of 29 and 14.7kD (P29 and P14.7) which can be further purified by preparative SDS/PAGE and hydrophobic chromatography, respectively. Amino acid composition analyses and immunoblotting of two-dimensional gels indicate that these are distinct but possibly related polypeptides. N-terminal analysis of P29 reveals it to be a previously undescribed cytokine mediator of monocyte function. A peptide having the sequence Gly Ala Ala Val Leu Glu Asp Ser Gln, corresponding to the native N-terminal sequence of P29, also exhibits MCF activity equivalent to that of the intact 29kD protein.

5 Claims, 11 Drawing Sheets

OTHER PUBLICATIONS

Ralph, P. et al., "Induction of Antibody Dependent and Nonspecific Tumor Killing in Human Monocytic Leukemia Cells," *Cell Immunology,* 71(2):215–223, 1982.
Le, J. et al., "Activation of Human Monocyte Cytotoxicity by Natural and Recombinant Immune Interferon," *Journal of Immunology,* 131(6):2821–2826, 1983.
Celada, A. et al., "Evidence for a Gamma–Interferon Receptor That Regulates Macrophage Tumoricidal Activity," *Journal of Experimental Medicine,* 160(1):55–74, 1984.
Eyster, M. E. et al., "Acid–Labile Alpha Interferon: A Possible Preclinical Marker for the Acquired Immunodeficiency Syndrome in Hemophilia," *The New England Journal of Medicine,* 309(10):583–586, 1983.
Jones, M. and Clouse, C. A., "Monocyte Cytotoxicity Factor (MCF) Production by a Human T–Cell Hybridoma," *Immunobiology,* 167: Abstract No. 365.
Nathan, C. F. et al., "Activation of Human Macrophages: Comparison of Other Cytokines with Interferon–γ," *Journal of Experimental Medicine,* 160:600–605, 1984.
Kleinerman, E. S. et al., "Lysis of Tumor Cells by Human Blood Monocytes by a Mechanism Independent of Activation of the Oxidative Burst," *Cancer Research,* 45(5), 1985.
Sadlik, J. R. et al., "Lymphocyte Supernatant–Induced Human Monocyte Tumoricidal Activity Dependence on the Presence of Gamma Interferon," *Cancer Research,* 45(5), 1985.
Proust, J. J. et al., "A 'Lymphokine–Like' Soluble Product That Induces Proliferation and Maturation of B Cells Appears in the Serum–Free Supernatant of a T Cell Hybridoma as a Consequence of Mycoplasmal Contamination," *Journal of Immunology,* 134(1):390–396, 1985.
Jones, C. M. et al., "Role of Bacterial Lipopolysaccharide and Lymphokine in the Regulation of Macrophage Activaiton: Correlates between Secretion of Plasminogen Activator and Tumor Lysis," *Immunobiology,* 166:410–427, 1984.
Grillot–Courvalin et al., "T–Cell Hybridomas," Michael J. Taussig, Ph.D. ed. 1985.
Grabstein, K. H. et al., "Induction of Macrophage Tumoricidal Activity by Granulocyte–Macrophage Colony–Stimulating Factor," *Science,* 232(4749):506–508, 1986.
Jones, C. M. et al., "Identification of a Human Monocyte Cytotoxicity–Inducing Factor from T Cell Hybridomas Produced from Sezary's Cells," *The Journal of Immunology,* 137(2):571–577, 1986.
Daemen, T. et al., "In Vitro Activation of Rat Liver Macrophages to Tumoricidal Activity by Free or Liposome–Encapsulated Muramyl Dipeptide," *Cancer Research,* 46:4330–4335, 1986.
Rosenberg et al., "A New Approach to the Adoptive Immunotherapy of Cancer with Tumor–Infiltrating Lymphocytes," *Science,* 233:1318–1321, 1986.
Goldstein, D., and Laszlo, J., "Interferon Therapy in Cancer: From Imaginon to Interferon," *Cancer Research,* 46:4315–4329, 1986.
Dialog Search Report.
Jones, C. M. et al. "Characterization of a Human Monocyte Cytotoxicity–Inducing Facor (MCF)," *Immunobiology,* 178:229–249, 1988.
Jones, C. M. et al., "Purification and Amino Acid Analysis of a Human Macrophage Cytotoxicity–Inducing Factor (MCF)," *Experimental Hematology,* 19:704–709, 1991.
Meltzer et al., "Macrophage Activation for Tumor Cytotoxicity: Regulatory Mechanisms for Induction and Control of Cytotoxic Activity," *Federation Proceedings,* 41(6):2198–2205, 1982.
Matthews, N., "Human Monocyte Cytotoxin Is Not Identical with Lymphoblastoid Lymphotoxin," *European Journal of Immunology,* 15:311–313, 1985.
Gregory et al., "Monocyte Procoagulant Inducing Factor: A Lymphokine Involved in the T Cell–Instructed Monocyte Procoagulant Response to Antigen," *The Journal of Immunology,* 137(10):3231–3239, 1986.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 9 amino acids
( B ) TYPE: amino acid
( C ) TOPOLOGY: linear ( i i ) MOLECULE TYPE: peptide ( x i ) SEQUENCE DESCRIPTION: SEQ ID NO:1:

```
Gly Ala Ala Val Leu Glu Asp Ser Gln
1               5
```

( 2 ) INFORMATION FOR SEQ ID NO:2:

( i ) SEQUENCE CHARACTERISTICS:
( A ) LENGTH: 9 amino acids
( B ) TYPE: amino acid
( C ) TOPOLOGY: linear ( i i ) MOLECULE TYPE: peptide ( x i ) SEQUENCE DESCRIPTION: SEQ ID NO:2:

```
Gly Ala Ala Val Leu Glu Asn Ser Gln
1               5
```

( 2 ) INFORMATION FOR SEQ ID NO:3:

( i ) SEQUENCE CHARACTERISTICS:
( A ) LENGTH: 5 amino acids
( B ) TYPE: amino acid
( C ) TOPOLOGY: linear ( i i ) MOLECULE TYPE: peptide ( x i ) SEQUENCE DESCRIPTION: SEQ ID NO:3:

```
Leu Glu Asp Ser Gln
1               5
```

PEPTIDES FOR INDUCING MONOCYTE CYTOTOXICITY IN DIAGNOSTICS

This application is a continuation-in-part of U.S. Ser. No. 07/624,053, filed Dec. 7, 1990 which is a divisional of Ser. No. 07/417,162, filed 4 Oct., 1989, now U.S. Pat. No. 5,112,948; which was a continuation in part of U.S. Ser. No. 06/917,983 filed 10 Oct., 1986, now U.S. Pat. No. 4,977,245. The government owns rights in the present invention pursuant to Public Health Services grant NIH R23-CA39441-01.

BACKGROUND OF THE INVENTION

1. Field of the Invention

The present invention relates to the fields of immunology and cancer therapy, and is directed to biological compositions and methods for inducing human monocytes to a cytoxic state. The invention concerns the purification and characterization of soluble factors, and particularly, of peptides, which induce human monocyte cytotoxicity and have utility in anti-cancer therapy.

2. Description of the Related Art

Immune protection of vertebrates is provided by a dual system that maintains two basic defenses against foreign invaders. These two defenses, termed cellular and humoral immunity, are adaptive and respond specifically to most foreign substances, although one response generally is favored. While cellular immunity is particularly effective against foreign tissue, cancer cells, intracellular viral infections and parasites, the humoral immune response defends primarily against the extracellular phases of bacterial and viral infections. Therefore, the cellular response is directed primarily against invading cells, while the humoral response is directed against primarily cell products, such as toxins. Moreover, whereas cellular immunity is provided by cells of the lymphoid system, humoral immunity is provided by proteins called antibodies that circulate through the fluid compartments of the body.

The dual nature of the immune system is generated from two separate populations of morphologically indistinguishable lymphoid cells called lymphocytes. While one class of lymphocytes, the T-cell lymphocytes, mediates the cellular immune response, the other class of lymphocytes, the B-cells, is responsible for the humoral immune response. Thus, when the organism is invaded by a foreign substance, for example an altered cell (e.g. viral transformed cell or tumor cell), some of the T-cells that recognize it are activated and initiate reactions that include binding to and eliminating the altered cells. On the other hand, when individual B-cells are activated, they differentiate to plasma cells that secrete specific antibodies directed against substances secreted by the foreign invader. For a review of the foregoing, see Hood et al., (*Immunology*, Second Edition, Benjamin/Cummings Publishing Company, Inc., Menlo Park, Calif., 1984).

While cells of B-lymphocyte lineage have found widespread clinical and industrial application in the generation of monoclonal antibodies, cells of T-lymphocyte lineage have proved of interest in part due to the numerous soluble factors they secrete. In the biological system, T-cell factors play an important role in modulating and activating various immune functions. Isolation and characterization of various T-cell factors has been the goal of many clinical research endeavors attempting to identify those factors which might be useful in treating a number of disease states, for example, in the treatment of tumor cells and viral infectious states. Of particular interest has been the recent characterization of a factor termed T-cell growth factor, or interleukin II, which is produced and secreted by effector $T_A$ cells. (See U.S. Pat. Nos. 4,401,756; 4,404,208; 4,407,945; and 4,473,642). When $T_C$ cells are stimulated by interleukin II, they undergo an effector phase and are stimulated to mature into killer T-cells which are capable of identifying and eliminating various target cells. As demonstrated by the above patents, interleukin II has become an important pharmaceutical agent in the treatment of various disease states.

Optimism spurred by the preliminary success of interleukin II has lead researchers on a quest to identify other immune-mediating factors having potential clinical applicability. However, this search has generally been hampered by the existence of numerous factors secreted by the same or similar cell types. Moreover, confusion often results from the general overlapping nature of the factor activities and often times from a lack of currently available test systems for identifying individual factor activities. Without highly sensitive test systems for identifying individual factor activities, the existence of a particular factor cannot be readily distinguished from other factor activities.

Recently, interest has been shown in identifying soluble factors which serve to stimulate human monocyte cytotoxicity. Monocytes are a phagocyte of the blood which, along with macrophages and polymorphonuclear leukocytes, bind and ingest foreign substances often prior to an antibody response. "Activated" monocytes have recently been shown to exert an antitumor activity. For example, Fischer et al. (*Cell. Immunol.*, 58:426–435, 1981) disclose that human peripheral blood monocytes can reproducibly lyse a variety of tumor cells. More recently, researchers have disclosed various factors thought to play a role in monocyte activation. For example, Kleinerman et al. (*Cancer Res.*, 45:2058–2064, 1985), discusses the activation of human blood monocytes by incubation with concanavalin A-stimulated lymphokine (macrophage-activating factor (MAF)), lipopolysaccharide endotoxin, and human recombinant gamma interferon. It was reported that gamma interferon, in the presence of endotoxin, was capable of activating monocyte tumoricidal activity. Moreover, MAF treatment exhibited a similar effect.

Other monocyte cytotoxicity promoting factors have been identified as well. For example, Le et al. (*J. Immunol.*, 131:2821–2826, 1983) has reported a T-cell hybridoma line capable of producing a macrophage activating factor with the ability to activate human blood. Monocytes to show enhanced cytotoxicity against a human colon adenocarcinoma line. However, this activity was found to be neutralized with specific antiserum to purified human interferon-gamma. These authors concluded that this MAF was in fact interferon-gamma.

More recently, Jones and Clouse (*Immunobiol.*, 167: Abstract No. 365, 1984) reported the use of lymphocytes from patients with Sezary's syndrome in the production of a human T-cell hybridoma line which is capable of producing a factor which stimulates human monocyte antitumor cytotoxicity. In contrast to the factor identified by Le et al., the factor reported in the Jones and Clouse publication was not inhibited by antibodies having specificity for interferon-gamma. Although the Jones and Clouse reference did observe that two molecular weight species having the biological activity was observable, the methodology used to identify this particular activity was not identified. Moreover, the methodology for identifying and isolating Sezary/T-cell hybridomas which secrete the particular factor was not disclosed. Clearly, not all Sezary/T-cell hybridomas are capable of producing monocyte stimulatory factors (See, e.g., Grillot-Courvalin et al., "Helper T-Hybridoma Produced By Fusion With Sezary Cells," in: *T-Cell Hybridomas,* ed. by M. J. Taussig, CRC Press, Inc., Boca Raton, Fla., 1985).

It is apparent from the foregoing references that, not only are there numerous factors potentially involved in the stimulation of human monocyte cytotoxicity, but additionally that these factor activities may be indistinguishable in previously available assays for detecting various cytotoxic actions. Moreover, as with other cytokines, the purification and characterization of monocyte cytotoxicity inducing factors has been hampered simply by their naturally low abundance in biological systems.

Accordingly, the present invention is directed to methods for accomplishing the isolation of particular discrete soluble factors which exhibit human monocyte cytotoxicity inducing activity. The present disclosure is further directed to the purification and characterization of these factors and to the preparation of T-cell hybridoma lines which produce these factors in vitro and thereby provide a ready source for isolating the factors. In that the novel factors of the present invention demonstrate a surprising ability to elicit an antitumor response by monocytes in vitro, similar to that possessed by interleukin II for lymphoid cells, it is believed that these factors will provide an important new addition to the antineoplastic armament of medical science.

SUMMARY OF THE INVENTION

The present invention is directed to compositions and methods for inducing human monocytes to a cytoxic state. The invention generally concerns the purification and characterization of soluble factors with human monocyte cytotoxicity inducing activity, referred to herein as MCF activity, and more particularly, to peptides with MCF activity. The factors and peptides of the present invention are contemplated for use in the treatment of cancer.

Substantially purified MCF, is a factor capable of inducing human monocytes to a cytotoxic state which comprises two polypeptides having molecular weights of about 29,000 Daltons (P29) and of about 14,700 Daltons (P14.7) when determined by polyacrylamide gel electrophoresis under the conditions as described herein. However, it is known that the migration of a polypeptide can vary, sometimes significantly, with different conditions of SDS/PAGE (Capaldi et al., *Biochem. Biophys. Res. Comm.,* 76:425, 1977, incorporated herein by reference). It will therefore be appreciated that under differing electrophoresis conditions, these molecular weights may vary.

The larger polypeptide of the human monocyte cytotoxicity inducing factor (P29) exhibits a molecular weight of about 29 kilodaltons on SDS polyacrylamide gel electrophoresis (SDS/PAGE) when the factor is obtained from cells grown in serum-free media. However, following gel filtration chromatography it exhibits a molecular weight of between about 78 and 63 kilodaltons, i.e., essentially the same as bovine serum albumin, when obtained from cells grown in media containing serum. In that bovine serum albumin itself has a molecular weight of approximately 68,000 Daltons, it is likely the case that this higher molecular weight species of MCF has an affinity for serum albumin. This would explain why, when obtained from cells grown in the presence of serum albumin, the higher molecular weight factor exhibits a molecular weight essentially indistinguishable from that of serum albumin.

The smaller polypeptide of MCF (P14.7) has an apparent molecular weight of approximately 11,500 Daltons when subjected to gel filtration chromatography under the conditions described herein. Again, as with gel electrophoresis, it will be appreciated that gel filtration chromatography does not provide an exact molecular weight determination. In this case, the monocyte cytotoxicity inducing activity elutes from such columns as a broad peak, corresponding to a molecular weight of approximately 11,500 Daltons. However, this molecular weight may vary with variations in conditions, for example, running buffer, exclusion limit, column size and the particular gel filtration methodology which is utilized.

A composition which includes one or both of the above factors may be further characterized by physicochemical and biological characteristics. For example, the composition and factor(s) retains biological stability following treatment at pH 2 for one hour. The term biological stability, as used herein, is defined as the retention of substantial biological activity following the indicated treatment as defined by the present disclosure. The composition similarly retains biological stability following treatment at 60 degrees Centigrade for one hour, and further retains biological activity in the presence of antiserum to interferon-gamma, interferon-alpha, or a combination of antisera to interferon-alpha and gamma. MCF activated monocytes retain biological activity in the presence of antiserum to Leu-llb plus complement indicating that the factor does not appear to activate NK cells, and following treatment by the enzymes Rnase, Dnase and trypsin. Biological activity is reduced following treatment by the enzyme chymotrypsin. The polypeptides of MCF can also be characterized according to their isoelectric points, P29 having an isoelectric point of 4.2, and that of P14.7 being 6.5.

Certain aspects of this study concern a continuous cell line which produces a factor as defined by the foregoing characteristics. In particular, a continuous cell line is provided which produces a factor capable of inducing human monocytes to a cytotoxic state, wherein the cell line is produced by a process which includes the steps of immortalizing human T-cells to produce continuous cell clones; identifying a clone which produces the factor; and culturing the clone to provide the continuous cell line.

The first step of immortalizing human T-cells to produce continuous cell clones is generally defined as providing human T-cells in a manner whereby they may be cultured continuously for an indefinite period. The most convenient manner for providing such continuous cell clones is through the development of a T-cell hybridoma. T-cell hybridomas are generally well known in the art and may be generated by a variety of well known methods. In general, such methods include fusing human T-cells with a second cell population which is sensitive to growth in a selective media and culturing the fused cells in the selective media to produce the continuous cell clones. Cells may be fused in numerous ways, for example, through the use of polyethylene glycol or Sendai virus.

In a preferred embodiment, the second cell population is a T-cell lymphoma population which has been selected for growth in 8-azaguanine. By selecting for T-cell lymphomas capable of growth in 8-azaguanine, a cell population sensitive to growth in HAT selective media is obtained. Those of skill in the art will recognize that other cell lines having other selective criteria may be utilized for fusion with human T-cells to provide the continuous cell clones. For example, additional T-cell lymphoma subtypes could be used to clone other subclasses of human T-lymphocytes. Moreover, drug sensitivities and other selective criteria can be generated using other approaches including, 6-thioguanine, oubaine or oncogenic transformation. Additionally, interspecies hybrids can be generated to allow for chromosomal localization.

However, fusion is not the only means of achieving immortalized human T-cells. For example, certain human T-cells are responsive to T-cell growth factor and may be immortalized by continuous culturing in the presence of T-cell growth factor (interleukin II). Additionally, certain human T-cells, for example, certain neoplastic T-cell lines are capable of continuous growth in cell culture as are certain transformed (e.g. virus transformed) T-cell lines. While most T-lymphotrophic viruses are toxic, it is known that HTLV-1, as well as portions of the EB virus genome, commonly utilized in B-lymphocyte transformation, can be used to transform and thereby immortalize, T-lymphocytes. All such continuously growing T-cells, and methods of providing continuously growing T-cells, are included within the scope of the present invention.

After obtaining the immortalized human T-cells in the form of continuous cell clones, a clone is identified which produces the monocyte cytotoxicity inducing factor. The crux of the successful practice of the present invention relies on the ability to identify clones which produce this factor rather than the numerous other immune regulatory and stimulatory factors known in the art. It is now believed that many hundreds of peptides, whose functions are unknown, are secreted by various activated T-cells. (see, e.g., Zurawski et al., *Science,* 232: 772–775, 1986). Moreover, depending on the particular T-cell which is immortalized, the number of clones positive for factor production may be quite low. Therefore, the assay must be not only highly specific for the present factor, but must be quite sensitive to the presence of small amounts of the factor, in order to successfully practice the present invention. Accordingly, the present disclosure is directed to an assay particularly adapted to identification of the present factor.

The final step of the present process is simply culturing the identified clone to produce the cell line. Where the immortalized human T-cell is achieved through hybridoma development, culturing will include simply culturing in an acceptable media. However, where the immortalized cell line does not involve cell fusion and instead requires the presence of a growth maintaining factor such as T-cell growth factor, culturing will require the inclusion of the particular growth factor.

In that it is believed that the factor of the present invention is secreted by a very small proportion of T-cells in general, it is a preferred embodiment of the present invention to employ Sezary cells as the T-cells to be immortalized. This is because it has been determined that a relatively large proportion of Sezary cells do in fact produce the present factor. However, in that it appears clear that not all Sezary cells produce the factor, the selection step is still required in order to identify clones producing the factor. However, if Sezary cells are unavailable, and one does not desire to screen the large number of clones which must necessarily be screened where T-cells in general are utilized, one may desire to use effector T-cells. It has been determined that a population of effector T-cells include a larger proportion of factor positive cells than do T-cells in general.

In a very general sense, the method of identifying a clone which produces the factor includes the steps of stimulating the clone with a T-cell mitogen to release lymphokines; culturing human monocytes together with appropriate target cells, for example, human cancer cells, in the presence of the released lymphokines; and detecting target cell lysis, wherein such lysis is indicative of the presence of human monocyte cytotoxicity inducing factor in the released lymphokines. As used herein, and as appreciated in the art, lymphokines is a generic term directed to any molecule having biological activity for modulating the immune system. A T-cell mitogen, as will be appreciated by those of skill in the art, is a molecule or a compound having the ability to stimulate the release of lymphokines from T-cells. In a preferred aspect of the present invention, the T-cell mitogen used is phytohemagglutin, commonly referred to as PHA. However, concanavalin A and other T-cell mitogens known to the art may be successfully utilized.

The second step of culturing human monocytes together with appropriate target cells in the presence of released lymphokines allows for the specific induction of monocyte cytotoxicity inducing factor where such factor is present in the released lymphokines. As noted previously, this particular step is quite important to the successful practice of the present invention and is disclosed in detail in connection with the disclosure of a preferred embodiment in a later section. Of course, to demonstrate that the present factor is indeed effective against human target cells, an appropriate human target cell is preferred. Useful target cells have been identified as the human myeloid leukemic cell line, K562 and also HL60, L5178Y and TU5 cells. This group of tumor targets includes both NK-sensitive and NK-resistant cells. However it is believed that numerous additional cell types may be employed, for example, melanoma, lung carcinoma and bladder cell tumors.

The final step of detecting target cell lysis is conveniently performed through the use of a radioisotope which is maintained extra or intracellularly when the target cell is in a non-lysed condition, and wherein the radioisotope is released into the surrounding media when the target cell is lysed. However, it will be appreciated that additional methods known in the art, and disclosed herein, may be used.

The present invention is additionally directed to a method for generating substantially purified monocyte cytotoxicity inducing factor, including both the P29 and P14.7 polypeptides, which comprises the steps of:

(a) stimulating a continuous cell line which produces the monocyte cytotoxicity inducing factor with T-cell mitogen to release the factor into the culture supernatant;

(b) subjecting the supernatant, or a fraction thereof, to affinity chromatography using a Matrex Gel Red A column;

(c) assaying the chromatography fractions to identify those fractions which retain a human monocyte cytotoxicity inducing factor;

(d) subjecting said monocyte cytotoxicity inducing factor-containing fractions to ion-exchange chromatography; and (e) identifying the chromatography fractions which contain human monocyte cytotoxicity inducing activity and collecting said fractions.

Practicing the method in this manner is preferred in that it will provide a factor-containing composition which is substantially purified with respect to biological activity as defined by the disclosed assay. However, it is believed that sufficient purity may be obtained by simply subjecting the culture supernatant to chromatography on a Matrex Gel Red A column (Amicon), i.e., performing steps (a) to (c), as above. To conduct such a purification step, one would pass the supernatant over the column in a low salt-containing buffer, such as 20 mM phosphate-buffered-saline (PBS), 0.15N NaCl, to bind the factor to the Matrex gel, wash the column to remove non-binding material, and then elute the bound fraction from the column with a buffer having an increasing salt concentration, such as PBS with a salt gradient of 0.15—1N NaCl.

As stated above, to achieve a more purified factor preparation containing both the P29 and P14.7 polypeptides, one may combine the Matrex Gel Red A column procedure with an ion-exchange chromatography step. To perform ion-exchange chromatography in this manner one would preferably include the steps of:

(a) dialyzing the monocyte cytotoxicity inducing factor-containing fractions from the Matrex Gel Red A column against a low salt-containing buffer;

(b) passing said dialyzed fractions over an ion exchange column in a low salt-containing buffer to bind the factor to the column;

(c) washing the column to remove non-binding materials; and (d) eluting bound material from the column with a high salt-containing buffer.

A preferred ion-exchange column for use in such embodiments is a DEAE column. However, other columns are contemplated to be of use, such as a Mono Q column (Pharmacia).

In further embodiments, the present invention provides methods to prepare substantially purified P27 or P14.7 polypeptides of human monocyte cytotoxicity inducing factor. The preferred starting material for the further purification of either P27 or P14.7 is the substantially purified MCF obtained following both Matrex Gel Red A and ion-exchange chromatography.

To obtain the MCF P27 polypeptide one would then subject the ion-exchange-eluted material to one-dimensional polyacrylamide gel electrophoresis, elute fractions from the polyacrylamide gel and identify the fractions having monocyte cytotoxicity inducing activity.

The preferred procedure for obtaining a substantially purified MCF P14.7 polypeptide involves subjecting the ion-exchange-eluted material to hydrophobic chromatography. To purify P14.7 in this manner one would include the following steps:

(a) prepare a sample of ion-exchange-eluted material in a buffer containing a high concentration ammonium sulphate solution;

(b) pass the sample in the high concentration ammonium sulphate over an octyl sepharose column to bind the factor to the column;

(c) wash the column to remove non-binding materials; and (d) elute bound material from the column with a buffer containing a low concentration ammonium sulphate solution and containing sodium dodecyl sulphate.

In using hydrophobic chromatography to further purify MCF P14.7, it is contemplated that the high concentration ammonium sulphate buffer used to prepare the sample will have an ammonium sulphate concentration of over 6M, and more preferably, of about 8M ammonium sulphate. To elute the bound P14.7 from the column one would use a buffer with a decreasing ammonium sulphate concentration, such a buffer with a gradient of 8-0M ammonium sulphate. It is also preferred that the elution buffer contain a more hydrophobic component, for example, a detergent such as Tween 20, or more preferably, SDS.

However, other combinations of hydrophobic columns and buffer systems are contemplated to be of use in accordance herewith. For example, one could use an RP8 column with acetonitrile/pyridine. Appropriate techniques for use with other hydrophobic columns, such as phenyl sepharose, will be known to those of skill in the art in light of the present disclosure.

In further and particularly important embodiments, the present invention is directed to novel MCF-derived peptides and to synthetic peptides with MCF activity. The inventor has determined the N-terminal amino acid sequence of MCF P29 to be:

Gly Ala Ala Val Leu Glu Asp Ser Gln (Seq id no:1)

The inventor determined that a synthetic peptide comprising this 9 amino acid sequence (termed MJ-2) is capable of activating human blood monocytes for tumor cytotoxicity. Variants of the 9 residue peptide with certain amino acid substitutions have also been shown to exhibit human monocyte cytoxicity inducing capabilities. A variant examined to date and found to have biological MCF activity was the peptide MJ-1 in which the single aspartate residue at position 7 had been replaced by asparagine. A 5-mer peptide, MJ-5, having the sequence Leu Glu Asp Ser Gln was also found to be critical for biological activity.

Therefore, in certain embodiments, the present invention is directed to the use of proteins or peptides of at least 5 amino acid residues in length, and having an apparent molecular weight of less than or equal to 29 kilodaltons, as determined by SDS polyacrylamide gel electrophoresis, the protein or peptide including at its amino terminus a sequence being selected from the group consisting of:

Gly Ala Ala Val Leu Glu Asp Ser Gln (seq id no:1);

Gly Ala Ala Val Leu Asp Asn Ser Gln (seq id no:2);

Leu Glu Asp Ser Gln (seq id no:3);

wherein Gly=Glycine (G); Ala=Alanine (A); Val=-Valine (V); Leu=leucine (L); Glu=Glutamate (E);

Asn=Asparagine (N); Ser=Serine (S); Gln=Glutamine (Q); and Asp=Aspartate (D).

The synthesis of synthetic peptides, such as those outlined above, using an automated peptide synthesizer, will be generally known to those of skill in the art in light of the present disclosure.

The peptides of the present invention are contemplated to be os use in a variety of different embodiments. For example, in important embodiments, it is believed that any one, or a combination of, the above peptides could be employed in any of the clinical or diagnostic embodiments described herein below. Moreover, the peptide sequences could be used to design corresponding oligonucleotide probes for use in the molecular cloning of the gene encoding the MCF P29 polypeptide.

Such cloning techniques are often employed in the art for the preparation of a so-called "recombinant" protein, which recombinant proteins may then be expressed in, and subsequently obtained from, recombinant host cells. "Cloning" the 29kD protein, refers to the process of obtaining a specific DNA molecule which encodes this protein, in a form distinct from other portions of DNA. To achieve this, one may screen a cDNA or genomic DNA library with, for example, an oligonucleotide probe or probes designed from a knowledge of the amino acid sequence of portions of the protein, such as the N-terminal sequence disclosed herein. Following the cloning of an appropriate DNA molecule, it may be inserted into any one of the many vectors currently known in the art and transferred to a prokaryotic or eukaryotic host cell where it may be used to direct the expression and production of the so-called recombinant version of the protein.

A synthetic peptide, termed MJ-2, having the sequence Gly Ala Ala Val Leu Glu Asp Ser Gln (seq id no:1) is shown herein to be capable of inducing the cytotoxic activity of human blood monocytes, from all donors tested, to a similar extent as the intact protein of 29kD. The use of this peptide, or an equivalent thereof, in any or all of the clinical embodiments for which MCF could be used is therefore contemplated. Indeed, the use of peptides in such embodiments is preferred for several reasons.

The advantages of using peptides in human therapy are many, and include, for example, the cost and relative ease of large scale synthesis as opposed to purification from natural sources; the invariant composition of the purified peptides obtained from different syntheses; and the elimination of the possibility that any other natural factors or compounds may be present which may adversely affect the human recipient despite their low concentration. Furthermore, peptides have preferable pharmacological properties such as the ease with which they can penetrate tissues and their low immunogenicity.

Accordingly, in prefered embodiments, it is contemplated that the use of a peptide of substantially less than 29kD in molecular weight will be advantageous. The present invention therefore concerns peptides of between 5 and about 100 amino acid residues in length, having at their amino terminus (N-terminus) an amino acid sequence corresponding to any one of the sequences set forth in seq id no:1, seq id no:2, seq id no:3, or a biologically functional equivalent thereof. Peptides of between about 5 and about 50 residues in length which terminate with such a sequence, or an equivalent thereof, are preferred; and peptides of between 5 and about 20 residues in length which terminate with such a sequence, or an equivalent thereof, are particularly preferred. Even more preferred, are peptides of at least 9 amino acid residues in length which peptides have at their N-terminus the sequence Gly Ala Ala Val Leu Glu Asp Ser Gln (seq id no:1).

As is generally understood in the art, modifications and changes may be made in the structure of a protein or peptide and still obtain a molecule having like or otherwise desirable characteristics. For example, certain amino acids may be substituted for other amino acids in a protein structure without appreciable loss of interactive binding capacity with other structures such as, for example, substrate molecules, enzymes or receptors. Since it is the interactive capacity and nature of a protein that defines that protein's biological functional activity, certain amino acid sequence substitutions can be made in a protein sequence (or, of course, its underlying DNA coding sequence) and nevertheless obtain a protein with like properties. It is thus contemplated by the inventors that various changes may be made in the sequence of the peptides disclosed herein without appreciable loss of their biological utility or activity.

In making such changes, the hydropathic index of amino acids may be considered. The importance of the hydropathic amino acid index in conferring interactive biological function on a protein is generally understood in the art (Kyte et al., *J. Mol. Biol.,* 157:105–132, 1982). It is known that certain amino acids may be substituted for other amino acids having a similar hydropathic index or score and still retain a similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein or peptide, which in turn defines the interaction of the protein with other molecules such as enzymes and receptors. It is known in the art that an amino acid may be substituted by another amino acid having a similar hydropathic index and still obtain a biological functionally equivalent protein. In general, the substitution of amino acids whose hydropathic indices are within ±2 is considered to be an appropriately conservative change. In the present case, it is contemplated that amino acid changes that are within ±1 will be preferable, and that changes within ±0.5 will be particularly preferred.

Substitution of like amino acids can also be made on the basis of hydrophilicity, as disclosed in U.S. Pat. No. 4,554,101, incorporated herein by reference. In U.S. Pat. No. 4,554,101, the following hydrophilicity values are assigned to amino acid residues: arginine (+3.0); lysine (+3.0); aspartate (+3.0±1); glutamate (+3.0±1); serine (+0.3); asparagine (+0.2); glutamine ( +0.2); glycine (0); (0±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In a similar manner to that described above, the substitution of amino acids whose hydrophilicity values are within ±2 is generally considered to be an appropriately conservative change. In regard to the present invention, is contemplated that amino acid changes that are within ±1 will be preferable, and that changes within ±0.5 will be particularly preferred.

Amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

It is further contemplated that the peptides of the present invention may be modified to render them biologically "protected". As is generally known in the art, biologically protected peptides have certain advantages over unprotected, i.e., unmodified, peptides when administered to human subjects. As disclosed in U.S. Pat. No. 5,028,592, incorporated herein by reference, a peptide which is protected, for example, through acylation of the amino terminus and/or amidation of the carboxyl terminus often exhibits an increase in pharmacological activity.

Bioactive peptides which contain an acetyl group bound to the N-terminus and/or an amido function bound to the C-terminus have been found to maintain biological activity, but to be less susceptible to acid hydrolysis. This is beleived to be due, in part, to the protecting groups playing a role in reducing the susceptibility of the protected peptide to enzymatic attack and degradation. Therefore, in further embodiments, the invention contemplates the use of pharmaceutical preparations of a protected peptide(s) comprising the active peptide in combination with pharmaceutically acceptable buffers, diluents, stabilizers and the like. For a listing of appropriate techniques and suitable pharmaceutical agent/additives compositions, one may wish to refer to *Remington's Pharmaceutical Sciences,* 16th ed., 1980, Mack Publishing Co., incorporated herein by reference.

In that it is believed that the monocyte cytotoxicity inducing factor of the present invention, and synthetic peptides with MCF-like activity, will be clinically useful in a manner similar to that identified for interleukin II and the various interferons, methods are additionally disclosed for clinical utilization and treatment of disease states using MCF. In addition to clinical applicability with respect to tumor treatment, as indicated by demonstrated in vitro efficacy in stimulating monocyte antitumor activity, it is believed that pharmaceutical compositions of the present invention will be useful in the treatment of infectious diseases, particularly those infectious diseases wherein the causative organisms reside in mononuclear phagocytes, for example, tuberculosis and leishmaniasis.

Additionally, it is believed that compositions included by the present invention will find diagnostic utility. Antiserum specific for MCF would be of value in determining blood levels of MCF, as well as documenting the ability of patients' mononuclear cells to produce MCF. Since MCF is produced by T-lymphocytes, and in particular, neoplastic T-lymphocytes, MCF will likely serve as a marker for diagnosis and/or evaluation of T-cell malignancies.

With respect to therapeutic utilization of MCF, one treatment protocol would include the ex vivo activation of a patient's mononuclear cells for reinfusion into the patients in a manner analogous to LAK cells as described by Rosenberg et al. (*J. Natl. Cancer Inst.,* 75:595, 1985, and *N. Eng. J. Med.,* 313:1485, 1985). For direct delivery of MCF to tissue macrophages, it is contemplated that MCF, or peptides with MCF activity, may be given by direct transfusion, encapsulated in liposomes, or could be incorporated into a viral transvecting particle for use in transduction in gene therpay protocols. Such techniques have recently been found to increase the efficacy and significantly prolong the half-life of related low molecular weight mediators. Liposome encapsulation can be accomplished in a number of manners, for example, as described by Fidler et al. (*Cancer Res.,* 36:3608, 1976) incorporated herein by reference.

Additionally, combination therapy employing MCF or peptides with MCF activity in combination with interleukin II, interferon, tumor necrosis factor and cytoxan, are contemplated. These additional agents may be obtained and employed in a manner known in the art as further disclosed herein.

It is further believed that pharmaceutical compositions which include MCF or peptides with MCF activity will find utility in direct infusion treatment in a manner similar to that utilized for interferon treatment. It is believed that dosage determination, as well as proper infusion techniques, is well within the skill of the art as exemplified by Goldstein et al. (*Cancer Res.,* 46:4315–4329, 1986), incorporated herein by reference. Moreover, in that interferons have found applicability in the treatment of various infectious disease states as noted above, it is believed that such utility will be applicable to MCF as well, for example, when employed as suggested by Nathan et al. (*J. Exp. Med.,* 160:600–605, 1984), incorporated herein by reference.

Diagnostic procedures, utilizing antibodies specific for MCF, may be employed in a manner similar to the current clinical test for acquired immune deficiency syndrome. Most conveniently, this would include a standard enzyme linked immunosorbent assay (ELISA), well known to those skilled in the art.

DETAILED DESCRIPTION OF THE PREFERRED EMBODIMENTS

Introduction

Figure 1:
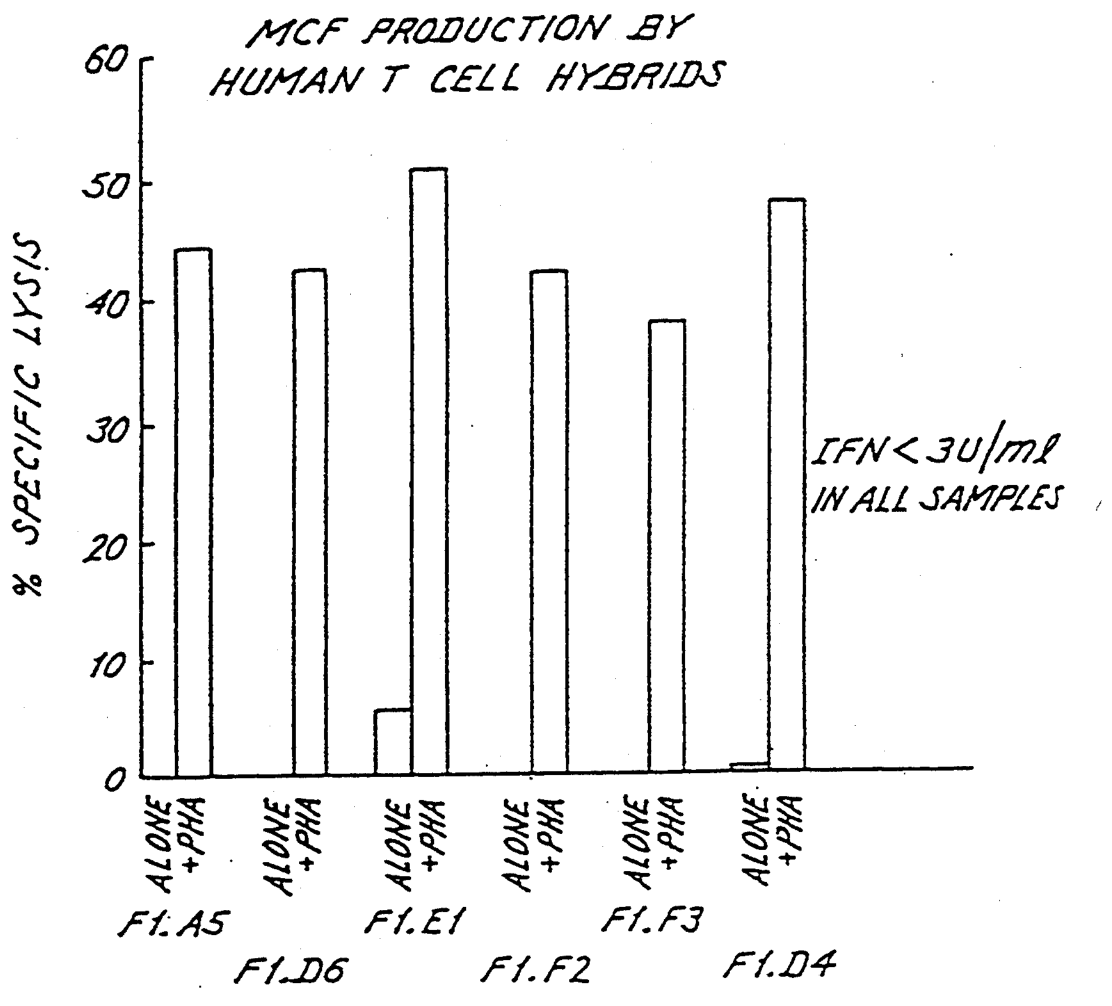
FIG. 1. Hybrid cells were adjusted to $1\times10^6$/ml and stimulated with 8 ug/ml PHA(+). PHA was added back to control (−) cultures, and both supernatants harvested by centrifugation. Monocyte cytotoxicity was measured as described herein with the exception that the monocyte monolayer was incubated overnight to allow for decay of NK cell activity. The monolayer was incubated for a second 24 hr period with dilutions of MCF containing supernatants. Dilutions represented are ¼ in a total test volume of 0.2 ml. The supernatant was washed away and the $^{111}$In-Ox-labeled targets, K562 were added (E:T,30:l). Microtiter plates were centrifuged 16 hrs later, and supernatants collected and counted. % specific release was calculated as described herein.

Concepts of monocyte activation for cytotoxicity have undergone a change from the "all or none" paradigm to the more precise concept of a discrete stepwise process. Our present understanding of monocyte activation has been addressed by Cohn (*Jrnl. Immunol.,* 121:813–816, 1978). Moreover it is generally recognized that activation is regulated by products of T-lymphocytes. Soluble mediators of mononuclear phagocyte activation have recently been reviewed by Nathan et al., supra.

From these studies and earlier reports, interferon gamma would appear to the most important if not the only regulator of cytotoxicity against microorganisms and has recently been identified as a migration inhibitory factor. However, other studies have suggested that colony stimulating factor (CSF I), and the interferons alpha and beta, may have roles in regulating secretory or proliferative functions. The present invention is directed to the perhaps surprising discovery that an additional factor, termed monocyte cytotoxicity inducing factor (MCF) by the present inventors also plays a role. In light of the present finding, it is likely that additional factors will be identified through the development of the individual assays particularly suited to identification of factor activities.

The MCF disclosed by the present invention is characterized biologically by an ability to stimulate monocytes to a cytotoxic antitumor state. While the precise function of MCF within the biological system is unknown, it is believed that it might play a role in affording specific activation of the cellular immune system. MCF appears to cause an increase in the synthesis and release of IL 1 by monocytes, which may act to either perpetuate the cytolytic state, to directly lyse susceptible tumor targets, or to induce cytostasis. MCF has no TNF, m-CSF, or IFN-like anti-viral activity. Similarly MCF has no activity when tested in the IL 1, IL 2, or m-CSF assays. Moreover, MCF was not directly cytotoxic for the targets K562 or L929, indicating that MCF has no lymphotoxin-like activity of its own. The factor is characterizable as having two molecular weight forms, one about 29,000 Daltons, and a lower molecular weight form of between 11,500 and 18,100 Daltons, depending on the particular molecular weight determination method utilized. It is emphasized that these two molecular weight forms exhibit indistinguishable biological activity in terms of monocyte activation. Therefore, the term MCF is meant to relate to either of these two molecular weight forms individually or in combination.

Sensitivity of MCF to the enzymes and metabolic inhibitors described herein are consistent with a conclusion that MCF is a peptide. For example, responses to metabolic inhibitors (actinomycin-D, puromycin, and cycloheximide), suggest that transcription of message is necessary and that messenger RNA for MCF does not persist. Because treatment of non-lectin-treated cells with puromycin did lead to production of MCF, and because total suppression of MCF could not be achieved with cycloheximide and puromycin, these data are consistent with either regulation of transcription by a repressor protein or its product, or at the level of translation, by stabilization of message.

MCF is most conveniently isolated through the preparation of a T-cell hybridoma employing Sezary cells isolated from an individual having Sezary's syndrome. Sezary's syndrome is characterized by a proliferation of leukemic helper T-cells, and is discussed in some detail by Broder et al. (*J. Clin. Invest.,* 58:1297–1306, 1976). Sezary's cells circulate in the peripheral blood and are known to provide T-cell help for immunoglobulin production. These cells are identified by their characteristic cerebriform nuclei, PAS positive vacuoles, and additionally by their surface marker phenotype (OKT3+, OKT4+, OKT8−, OKIal−(+)). Helper function has been defined by the ability of Sezary cells to stimulate polyclonal IgG production by B lymphocytes and by their production of MIF. Although lymphokine production does not necessarily segregate exclusively to any one subclass of T cells, Sezary's cells most probably represent a homogeneous clonal expression of one particular subclass of human T-lymphocytes which can be studied for production of lymphokine mediators uncontaminated by other T-cells.

The use of Sezary cells, as noted above, is not crucial to the practice of the present invention in that it is believed that MCF production is a feature common to lymphocyte populations in general. However, not all cells of a particular T-cell population produce MCF. Thus, where a general T-cell population is utilized, only a very small percentage of cells are likely to produce MCF. In the case of Sezary's cells, it appears as though MCF production is a more generalized phenomenon. Therefore, Sezary's cells are preferred in that T-cell hybridomas produced from Sezary's cells provide clones wherein there is a much greater likelihood that any one particular clone would produce MCF. Conversely, it is likely that when general T-cell populations are employed for hybridoma production, a substantial number of clones will likely have to be screened before a positive clone is identified. However, where Sezary's cells are not available, one may employ helper T-cells, in that it appears that helper T-cell populations contain a sufficient percentage of positive cells to avoid the exhaustive screening which would be necessitated by employing general T-cell lymphocyte populations.

Recently, strong evidence has been presented that interferon-gamma is the major mediator of macrophage/monocyte activation, and may be identical with the lymphokine macrophage activation factor (MAF). Interferon-gamma has also been described as the mediator of inhibition of mononuclear phagocyte migration and hence may be migration inhibition factor (MIF). However, it is known that activated Factor B of the alternative complement pathway (Bb), plasminogen activator (PA), and other products of monocytes will inhibit migration. Nathan et al., supra, have recently reviewed the range of mediators of mononuclear phagocyte activation.

The production of lymphokines by malignant T-cells is important in understanding host defense in conditions with chronic courses such as Sezary's syndrome and may reflect production of such mediators by non-malignant counterparts in the normal host. In developing the present invention, attempts were made to expand Sezary cells with interleukin II (IL-2), but these attempts were unsuccessful. Similar results have been reported by other groups, and have been attributed to the lack of IL-2 receptor expression or proliferation of Sezary cells by non-IL-2 dependent means. Clearly, as additional cell lines are screened for MCF production, cells will be identified which may be immortalized through the inclusion of growth factors in the cell growth medium, thus avoiding the need for hybridoma development.

Previously, hybridization has been utilized to perpetuate subclasses of murine T-cells and this technique was applied to Sezary's cells for the present invention. Other groups have employed Sezary cell hybridomas to study BCGF (B-cell growth factor) production by Sezary's cells. In the present invention, six cell lines were obtained by hybridization and all were capable of inducing human blood monocytes to become cytotoxic for the myeloid leukemia target, K562. For further study, one hybrid, FtF3, was selected whose phenotype (OKT3+, 4+, 8−, OKII1−, sIgG−) was identical to the parent Sezary's cell. It is of interest that all lines produced a lymphokine capable of inducing monocyte cytotoxicity (MCF). This probably results from positive selection of fusion partners since similar hybridization experience using whole murine T-cell populations have given rise to much smaller percentages of clones with MAF-like function.

Supernatants from PHA-stimulated FtF3 induced human mononuclear cytotoxicity but contained no detectable interferon. Antisera to native interferon-gamma when added in excess to MCF having no antiviral activity produced only a 10–15% decrease in specific lysis of the target K562. Moreover, when formal titrations of the anti-IFN-gamma antisera were carried out using the constant antibody method previously described as being optimal for the detection of cross-reactivity with IFN-gamma, no neutralization titer could be determined. In contrast, treatment with the antisera to interferon-alpha caused a small increase in specific release. Addition of both antisera together produced no change in specific lysis. Both antisera were produced against partially purified native human interferons. In the case of the antisera to interferon-gamma, some cross-reactivity may be detected in that an MCF-like molecule could have been present in the preparation used to raise the antisera which was previously not recognized.

The development of a series of monoclonal antibodies which are capable of differentially blocking antiviral or MAF activity of interferon-gamma, respectively, has been described by Schreiber. In particular, monoclonal antibodies directed against the C-terminus of recombinant interferon-gamma were reported to block MAF but not the antiviral activity of the recombinant interferon-gamma, while the antibodies to the N-terminus of recombinant interferon-gamma blocked antiviral but not MAF activity. Therefore, these findings could be consistent with an interpretation that MCF was an altered interferon species produced by a T-cell leukemia-derived hybridoma. However, the fact that MCF has recently been determined by the present inventors to be produced by normal effector T-cells, appears to rebut this theory.

These issues were further approached by direct comparison of the physicochemical properties of MCF and native interferon-gamma. Unlike interferon-gamma, MCF was stable at pH 2 but was partially inactivated at pH 8 and was much more stable than interferon-gamma. IFN- was inactivated by trypsin, in contrast to the effect of this enzyme on MCF. These findings would support the concept that MCF is not an altered interferon-gamma which has lost antiviral, but not MAF activity, because interferon-gamma lost both MCF and antiviral activity with both low pH and heat treatment.

MCF is a lymphokine distinct from TNF, IL 1, IL 2, m-CSF or IFN.MCF has no activity when tested in assays for IL 1, IL2 or M-CSF. MCF had no TNF, m-CSF, or IFN-like antiviral biological activity when compared to RTNF, purified human m-CSF, IFN gamma or alpha/beta, respectively. In addition, MCF had no cross reactivity with m-CSF in the radioimmunoassay for m-CSF.

Gel filtration chromatography of concentrated supernatants from cells raised in the presence of serum, revealed two molecular weight species, one with a molecular weight of 64,000 daltons which co-eluted with the major protein peak, bovine serum albumin, and a second with a molecular weight of 11,500 daltons. Although yields from our Bio-Gel P-100 column have been low, these values differ from the molecular weight of 50,000 reported for native human interferon-gamma when chromatographed under similar conditions. When such cells were cultured in serum-free media, the higher molecular weight species migrates at about 29 kD upon SDS gel electrophoresis.

MCF was found to bind to Matrex Gel Red A (procion-red agarose; Amicon) and eluted with 1-N NaCl. Similar results have been reported for native interferon-gamma. MCF eluted from Matrex Gel Red A was electrophoresed under reducing conditions on a 15% SDS-PAGE gel. Two molecular weight species were identified. The first had a molecular weight of approximately 29,000 daltons when produced in serum-free media and the second had a molecular weight of about 14,700 Daltons. The specific activity was 610 MCF units/mg protein and 1350 MCF units/mg protein, respectively. Yields from this procedure have been excellent with recoveries greater than 90%, despite treatment with SDS.

Electrophoresis under reducing conditions followed by dialysis to remove SDS has resulted in each case in a diminution of biological activity associated with the higher molecular weight form and greater recovery of the lower molecular weight form.

Further and important aspects of this study concern the delineation of N-terminal sequence of P29 and the inventor's discovery that synthetic peptides corresponding to this sequence, or variants thereof, exhibit MCF activity. The N-terminal amino acid sequence of MCF P29 was found to be: Gly Ala Ala Val Leu Glu Asp Ser Gln (seq id no:1). A synthetic 9mer peptide having this sequence is capable of activating human blood monocytes for tumor cytotoxicity to a similar extent as MCF itself. A further peptide with the substituted sequence Gly Ala Ala Val Leu Glu Asn Ser Gln (seq id no:2), and a shorter peptide with the sequence Leu Glu Asp Ser Gln (seq id no:3) also have MCF activity.

The peptides of the present invention are contemplated to be os use in the variety of clinical and diagnostic embodiments proposed for MCF itself. The use of peptides in such embodiments is actually preferred for various reasons, such as the low cost and relative ease of large scale preparation, and the reliability of the product; the ease with which peptides can penetrate tissues; and their low immunogenicity. As mentioned above, the peptides may be further modified prior to administration by the addition of a stabilising group to their N- or C-termini, for example, by acylation or amidation.

It is contemplated that peptides in accordance with the present invention may be synthesized by any of the automated methods currently known in the art, for example, as disclosed hereinbelow. Alternatively, they may be produced as a fusion protein by employing the techniques of genetic engineering and expression in host cells. Such techniques are generally known in the art and used to produce proteins or peptides linked to various proteins, or parts of proteins, such as, for example, β-galactosidase or ubiquitin. The fusion proteins may then be purified by any of the standard techniques known in the art. The fusion proteins may be used themselves, or the peptides released from the remainder of the fusion prior to use. The latter technique is particularly employed where the genetic construct has been so designed to include a protease sensitive site, to allow cleavage by exposure to a free or immobilized protease.

EXAMPLES

1. Isolation of Sezary's cells

Mononuclear cells were isolated from 60 ml whole blood from a patient previously known to have Sezary's syndrome. Mononuclear cells were isolated by centrifugation over Ficoll-Hypaque (Pharmacia, Piscataway, N.J.). $7.5\times10^7$ cells having a phenotype of 87% 0KT 3+, 77% 0KT 4+, and 12% 0KT B+ were recovered from the F/P centrifugation and applied to a 35 ml gradient of Percoll (Pharmacia) according to the method of Gemlig-Meyling and Waldman (*J. Immunol. Method.*, 33:1, 1980, incorporated herein by reference). Briefly, the gradients were made by mixing 168 ml Percoll with 144 ml 2× PBS, and centrifuged for 40 min at 21,000×g in a Beckman Model 71 centrifuge with a SS-34 fixed angle rotor. The cells were suspended in 5 ml of Hank's balanced salt solution (HBSS), layered gently on the gradient, centrifuged at 100×g for 20 min at 20° C. in a swinging bucket rotor. Standard density marker beads (Pharmacia) were loaded on a companion gradient.

Three distinct "bands" were recovered from Percoll. At the interface between the Percoll and sample were $1.5\times10^6$ cells, the majority of which were polymorphonuclear leukocytes, and were discarded. Band I, 2 cm below the interface contained $1.9\times10^7$ cells which when studied by flow microfluorometry (FMF) were 90.2% 0KT 3+, 80% 0KT 4+, and 47% 0KT 8+, and were morphologically small lymphocytes. Band II, located 5 cm below the interface contained $7.8\times10^6$ cells, which were 97% 0KT 3+, 96% 0KT 4+, and 17% 0KT 8+. Microscopically, these cells were larger and had cerebriform nuclei. 38% of the total cells applied to the gradient were recovered.

Cells isolated in Band II were washed and resuspended at $5\times10^5$ cells/ml in RPMI 1640 with 10% fetal calf serum (FCS). Aliquots of these cells were cultured with 10 units/ml final concentration of interleukin II from the Gibbon ape cell line NLA-144. These cells failed to divide or incorporate 3H-Tdr after 72 hrs of culture thus demonstrating a lack of IL-2 responsiveness.

Preparation of 8-azaguanine Resistant T-lymphocytes

Since these particular Sezary's cells were not capable of indefinite sustained growth in tissue culture, it was decided to prepare a continuous T-cell hybridoma line by fusing the Sezary's cells with a T-lymphocyte population which has been conditioned to grow continuously in tissue culture. To achieve hybrid selectability, it was first necessary to select a cell population which was sensitive to HAT selection medium. This was accomplished through the preparation of an 8-azaguanine-resistant T-lymphocyte population.

It has been determined that certain commercially available T-lymphocyte cell lines are to be preferred over others. CCRF-CEM is a cell line obtainable from the ATCC which, due to its apparent genetic stability, is to be preferred in generating hybridomas of the present invention. Two additional cell lines, MOLT and Jurkat, have been found to be genetically unstable upon drug selection and therefore unsuitable. However, the techniques of the present invention are applicable to any genetically stable T-cell lymphocyte or other cell type which can form a stable fusion product with T-cells and which is capable of continuous growth in culture. Determination of the foregoing criteria is within the skill of the art and the scope of the present disclosure is not limited to the preferred embodiment employing CCRF-CEM.

To generate 8-azaguanine resistant CCRF-CEM, cells were obtained from the American Type Culture Collection and grown in RPMI 1640 with 10% FCS. CEM was grown in increasing concentrations of 8-azaguanine primarily according to the method of Okada (*Proc. Natl. Acad. Sci.,* 78:7717, 1981, incorporated herein by reference). However, beginning with a concentration of 2 uM, the dose was doubled every 2 days until a dose of 16 uM was reached at which time the dose was doubled every 10 days until a dose of 100 uM was reached. After 6 weeks the cells were recloned and tested for their ability to grow in HAT containing media (hypoxanthine, aminopterin, and thymidine), and subjected to flow microfluorometry.

3. Generation of T-cell Hybridomas

T-cell hybridomas were formed between Sezary cells, isolated as described in section 1 above, and the 8-azaguanine-resistant, HAT-sensitive CEM T-lymphocyte line (CEM.8aza$^r$.C), prepared as described in section 2 above. In particular, $7.5\times 10^6$ cells from Band II of the Percoll gradient fractionation of patient's mononuclear cells were subjected to flow microfluorometry and light microscopic examination. These cells were hybridized to an equal number of CEM.-8aza$^r$.C using polyethylene glycol (mol wt 1000, Sigma, St. Louis, Mo.) as described by Jones, C. M., "T-cell Hybridomas Producing Macrophage Activation Factors," In: T Cell Hybridomas, Ed.: M. Taussig, CRC Press., Inc., Boca Raton, Fla., 1985, pp. 56–68, incorporated herein by reference. The fused cells were cultured for 24 hrs in RPMI 1640 with 10% FCS prior to addition of HAT-containing medium (hypoxanthine $1\times 10^{-4}$M, aminopterin $4\times 10^{-5}$M, and thymidine $1.6\times 10^{-5}$M). Colonies were selected after 1 month in HAT media and cloned by limiting dilution.

Individual hybridoma clone colonies which were isolated by this procedure were adjusted to a culture density of $5\times 10^5$ cells/ml and stimulated with 16 ug/ml phytohemagglutinin (PHA; Miles-Yeda, Rehovot, Israel) for 24 hours to stimulate lymphokine production. Thus, hybridoma clones were screened for positive MCF production by mitogen stimulation followed by subjecting the resultant hybridoma supernatants to biological screening in the human monocyte cytotoxicity assay, which is discussed in detail below.

The human T-cell hybridoma was also successfully maintained in 5% fetal calf serum (FCS), then grown in serum free media for at least 24 hours after stimulation by phytohemagglutinin (PHA). Either tissue culture media not supplemented by serum, or a serum-free media described by Sachs, *L., Clin. Exp. Immunol.* 33:495, 1978 and incorporated herein by reference, will support this growth for a limited time span. This cell growth procedure permits analysis of MCF prepared in serum-free conditions.

In particular, supernatants of stimulated and unstimulated clones were incubated 20 hours with the monocyte monolayer. Serial dilutions of the supernatant were made to quantitate MCF in each sample. The data in FIG. 1 show that all six clones produce a factor(s) which induces human monocytes to kill K562. Their phenotypes were studied by FMF and two clones, FtF3 and FtA5, were uniformly 0KT 3+, 4+, and were 0KT 8− and OKMT 1−, and IgG−.

Table 1 demonstrates the results obtained when supernatants from two representative MCF-producing hybridomas, FtA5 and FtF3, were subjected to the in vitro monocyte cytotoxicity assay. Cytotoxicity was measured by adding a fixed input of supernatant (25, 50 and 100 vl.) to a total test volume of 0.2 ml.

TABLE I

| | Specific Cytotoxicity Induced By Hybridoma Supernatants | |
|---|---|---|
| Hybrid | Input (ul) | % Specific Lysis |
| FtA5 | 25 | 10.3 |
| | 50 | 25.1 ± 6.9 |
| | 100 | 38.3 ± 8.4 |
| FtF3 | 25 | 11.1 |
| | 50 | 26.2 ± 10.4 |
| | 100 | 37.7 ± 6.8 |

4. Human Monocyte Cytotoxicity Assay

As noted above, successful practice of the present invention rests on the ability to successfully identify MCF activity in an in vitro assay which has been designed to distinguish MCF activity from the numerous other lymphokine activities produced by T-cells. The assay described below has been derived in part from an assay method reported by Koren and his associates (Fischer et al., *Cell Immunol.,* 58:426, 1981). However, the assay as described in the Fischer et al. reference was found to be unacceptable in that it is not designed to measure lymphokine induced cytotoxicity and does not eliminate natural killer cell activity. It, therefore, must be modified as follows.

Human monocyte enriched leukopaks were obtained as a byproduct of the platelet donor program at M. D. Anderson Hospital, and were prepared with an IBM Model 2997 Cell Separator. Only healthy volunteer donors were used. All volunteer donors signed an informed consent, and the protocol was approved by the Committee for the Protection of Human Subjects, University of Texas Health Science Center. Mononuclear cells were prepared by centrifugation over Ficoll/Hypaque. Monocyte monolayers were prepared by adherence to 96-well flatbottom plates previously coated with human serum as described by Golightly et al. (*Blood,* 61:390, 1983, incorporated herein by reference), and allowed to adhere to the serum coated plates for 15–30 mins followed by vigorous washing with warm (37° C.) Hank's balanced salt solution. This resulted in a confluent monolayer of >95% esterase positive cells. The monolayer was incubated overnight to allow for decay of residual natural killer activity before addition of lymphokine preparations on day 2. The monolayers were incubated with lymphokine for 20 hrs, washed, and the $^{111}$In-Ox labeled K562 added as targets.

The $^{111}$In-Ox labeled K562 target cells were prepared by the method of Wiltrout et al. (in: *Manual of Macrophage Methodology*, Ed. H. B. Herscowitz et al., Marcel Dekker, Inc., N.Y., pp 337–344, 1981, incorporated herein by reference). The effector to target ratio was 30:1. Spontaneous release averaged 15% (7–20%) in greater than 50 experiments. LPS (Lipopolysaccharide) free RPMI 1640 (M. A. Bioproducts, Walkersville, Md.) with 10% heatinactivated AB-negative human serum (FLOW Laboratories, Arlington, Va.) was used throughout the assay procedure. After 18 hrs incubation of monocyte monolayer with target, the plates were centrifuged and supernatant was removed and cpms were counted in a Beckman Biogamma 2000. Specific release was calculated as described by Wiltrout, supra. Units of MCF activity were calculated as described by Lohmann-Matthes (Kniep et al., *J. Immunol.*, 127:417, 1981). 20% specific release equals 1 unit of MCF. Other tumor targets used were HL-60, L5178Y and TU5 (Table V).

The primary distinction between the present assay and the one described by Fischer et al., is the finding that it is absolutely crucial that LPS-free media be utilized in order to distinguish the MCF activity from interfering activities. For the particular activity investigated by Fischer et al., the use of LPS-free media was not crucial in that it is noted by those authors that similar activities were observed regardless of whether LPS-free media was utilized. However, with respect to MCF, when LPS-containing media is used, a spontaneous release of label occurs and induction of lymphokine (MCF) directed cytotoxicity cannot be measured.

5. Deposit of Representative Sezary cell Hybridomas with the American Type Culture Collection By the foregoing procedures, six hybridoma clones were identified whose supernatants exhibited MCF activity. Two were chosen for further physiochemical and biological characterization. It has been determined that those two hybridomas, designated Ft.A5 and Ft. F3, both secrete the same MCF biological profile, as determined by the characterization criteria disclosed herein. Accordingly, one of these hybridomas, Ft. F3, has been deposited with the ATCC and accorded ATCC reference number HB9713.

6. Characterization of MCF

A. MCF is Antigenically Distinct From Interferon Gamma

1) Generation of MCF

MCF was generated by stimulating $5\times10^5$, $1\times10^6$, $2.5\times10^6$, or $5\times10^6$ FtF3 or FtA5 cells/ml with 2, 4, 8, 16, or 32 ug/ml PHA (Miles-Yeda, Rehovot, Israel) in RPMI 1640 with 1, 2.5, 5, or 10% FCS (Hyclone, Sterile Systems, Logan, Utah) for 24, 48, or 72 hrs. Unstimulated controls were grown with each to which an equal amount of PHA was added at the end of incubation. The cells were centrifuged, and the supernatants filter-sterilized, and stored at −30° C. For characterization and purification, MCF was then prepared by stimulating $1\times10^6$ cells/ml in RPMI 1640, 1% FCS with 8 ug/ml PHA for 24 hrs, centrifuged, and filter sterilized. This routinely gave approximately 40 U/ml activity. Unstimulated controls to which PHA was added back were used in all experiments.

MCF was also generated in serum-free media. FtF3 cells were first grown in RPMI 1640 containing 5% FCS. Cells were then washed twice with Hanks balanced salt solution (HBSS) and once with RPMI 1640. Cells were resuspended at a concentration of $1\times10^6$/ml or $3\times10^6$/ml in either RPMI 1640 containing 10, 5, 1, or 0.1% heat-inactivated, AB-negative human serum, RPMI 1640 alone, or a serum-free media described by Sachs (*Clin. Exp. Immunol.*, 33:495, 1978, incorporated herein by reference). Phytohemagglutinin (PHA) was added to a final concentration of 0, 0.5, 1.0, 2.0 or 4.0 micrograms/mi. Supernatants were collected at 24 and 48 hours, filter sterilized, and stored at −70° C. Satisfactory growth could only be maintained in RPMI 1640 having at least 5% fetal calf serum. However, after FtF3 had been conditioned to grow in media having 5% FCS, this cell line was capable of producing MCF under serum-free conditions as described herein. The total units of MCF recovered were scarcely different among the serum-containing medias or RPMI alone. The serum-free media of Sachs resulted in a decrease in MCF production of 5 to 10 U/ml. In addition, an increase in cell concentration from $1\times10^6$ cells/ml to $3\times10^6$ cells/ml did not increase levels of MCF production which is likely the result of decreased viability at higher cell density.

2) Interferon Assay

Human interferon activity was measured as inhibition of plaque formation by Sindbis virus on WISH cells as described by Baron et al. (*Infect. Immun.*, 32:449, 1981). Sindbis virus, human alpha, beta, and gamma interferons were prepared by Drs. Samuel Baron and Marlyn Langford, University of Texas Medical Branch, Galveston, Tex. WISH cells were obtained from Drs. Baron and Langford. Using this plaque inhibition assay, interferon was not demonstrated in supernatants of FtF3 and FtA5.

3) Treatment of IFN-gamma and MCF With Antisera to Various Interferons

Antibody to a partially purified preparation of native human gamma interferon (Langford et al., *J. Immunol.*, 126:1620, 1981), a 20 peptide N-terminal fragment of recombinant gamma interferon (Johnson et al., *J. Immunol.*, 129:2357, 1982) and human alpha interferon (Langford et al., supra) were prepared as described in the referenced articles. In initial experiments, 40 Units of MCF or 100 U IFN-gamma in 1 ml RPMI 1640, 1% FCS were incubated with 100 U of each of the antisera above alone or in combination at 4° C. for 30 min, 1 hr, and 4 hr. Following this incubation, serial dilutions of the IFN or MCF were made in RPMI 1640, 10% FCS and residual macrophage activating factor activity measured in the MCF assay.

27 U/ml of partially purified MCF were diluted ½ (13.5 U), ¼ (6.75 U), and ⅛ (3.375 U). Serial half-log dilutions were made of these dilute MCF, and the predicted number of units were confirmed by measurement in the MCF bioassay. Next, 27 U/ml of partially purified MCF were subject to serial half-log dilutions up to a final dilution of ⅛ 100 U, 50 U, or 25 U of each of the anti-IFN-gamma, antisera was added to each of these MCF dilutions and incubated for 1 hr at 25° C. Residual MCF activity was calculated in the constant antibody titration as recommended by Kawade (*J. Ifn. Res.*, 4:571-584, 1984). Units are expressed as described by Lohmann-Matthes (Kniep et al., supra).

Results from two representative sets of experiments are summarized in Table II. Anti-interferon-alpha produced no significant change in specific release. On the contrary, the presence of this antisera during the activation has consistently produced small increases in specific lysis. The antibody to a partially purified preparation of native human interferon-gamma (SEA-activated human PBL) produced a decrease of only 15% and 10% specific lysis. Antisera to the 20-peptide N-terminal fragment of recombinant interferon-gamma or to a combination of interferons alpha and gamma failed to neutralize MCF. The antisera themselves produced only small changes in spontaneous release of label from the target K562 when added in place of the activating agent (spontaneous release=22.6% with media and monocytes alone; specific release=−13.2% with anti-IFN-alpha, =4.66% with anti-IFN-gamma native, and =8.4% with anti-IFN-gamma N-terminus.) More importantly, IFN-gamma in amounts up to 1000 U/ml final concentration increased specific lysis only 6.2%. Because IFN-gamma did not produce significant activation for cytotoxicity in the present assay, direct comparison with MCF could not be performed.

TABLE II

Treatment of MCF with Antisera

| Treatment | % Specific Lysis Exp 1 | Exp 2 |
|---|---|---|
| untreated | 54.6 ± 3.8 | 29.8 ± 5.4 |
| anti-IFN-alpha | 57.6 ± 5.0 | 35.8 ± 4.2 |
| anti-IFN-gamma (native) | 40.6 ± 3.8 | 19.9 ± 8.5 |
| anti-IFN-gamma N-terminus | | 26.5 ± 8.0 |
| anti-IFN-gamma (native) + anti-IFN-alpha | 48.89 ± 5.3 | |

In order to confirm that increasing concentrations of antibody relative to MCF units would not affect induction of cytotoxicity, the following experiments were performed. Serial checkerboard dilutions of 27 U/ml partially purified MCF were carried out as described above. In each experiment, 100, 50, or 25 U of the anti-IFN-gamma antibodies were added separately to MCF dilutions and residual MCF units were measured. The results summarized in Table III demonstrate that 100 U anti-IFN-gamma native reduced total bioassayable units by 7 U/ml. This is consistent with preceding experiments. Addition of 50 U/ml anti-IFN-gamma (native) and all inputs of anti-IFN-gamma N-terminus caused an increase in bioassayable units.

TABLE III

Treatment of MCF with Anti-IFN-gamma by the Constant-Antibody Technique

| Input Ab (U/ml) | anti-IFN gamma (native) | anti-IFN gamma-N-terminus |
|---|---|---|
| 0 | 27 | 27 |
| 25 | 28 | 39 |
| 50 | 58 | 46 |
| 100 | 20 | 40 |

FtF3 and FtA5 MCF were also capable of activating murine peritoneal exudate macrophages for cytotoxicity against the target L5178Y. The presence of LPS did not appear to augment cytotoxicity induced by these lymphokines.

B. MCF is Distinct from IL 1, IL 2, TNF and m-CSF

1) Measurement of IL 1, IL 2, TNF and CSF Biological Activity

IL 1 activity was measured using the DIO.G4.1. cell line as described by Kaye and Janeway (*J. Immunol.*, 133:2291, 1984). IL 2 activity was measured as described by Bonnard, using cultured human T-cells (*Cell. Immunol.*, 51:390, 1980). TNF activity was measured by direct cytotoxicity against L929 cells as described by Gately and Mayer (*J. Immunol.*, 116:669, 1976). M-CSF was measured by both murine bone marrow colony formation (Waheed and Shadduck, *Exp. Hematol.*, 17:61, 1989; Shadduck and Waheed, *Ann. N.Y. Acad. Sci.*, 554:156, 1989) and by radioimmunoassay specific for purified human M-CSF.

2) Addition of Lymphokines to MCF Assay

Purified human IL 1 (alpha plus beta), rIL la, rIL lb, (Cistron Biotechnology, Pinebrook, N.J., USA), rIL 2 (Genzyme Corp., Boston, Mass., USA), RGM-CSF, or purified m-CSF (Waheed and Shadduck, supra), was added to the human monocyte cytotoxicity assay in order to determine the ability of lymphokines other than MCF to activate monocytes for tumor cytotoxicity. Antibody to a partially purified preparation of native human IFN-gamma, a 20 peptide n-terminal fragment of rIFN-gamma, and human IFN-alpha were used, and neutralization was carried out using the constant antibody method as previously described by Jones et al. (*J. Immunol.*, 137:571, 1986). Anti-serum to purified M-CSF, capable of neutralizing 0, 100 and 1,000 units/ml was added to a preparation of human MCF containing 33 U/ml. These were incubated one hour at room temperature. Resultant supernatants were tested in the MCF biological assay.

Using K562 as a cytotoxicity assay as previously determined, IFN-alpha/beta had no, and IFN-gamma only slight activity. Neither IL 1 or IL 2 had any activity in the MCF assay. Anti-sera to m-CSF failed to neutralize MCF activity. The CSF's had effects different from MCF. They caused monocyte cell division, altering the effector to target ratio and causing cells to assume a rounded morphology. MCFs by contrast did not cause cell division, but induced cytotoxicity and caused the cells to assume a macrophage-like morphology. The details of the effects of cytokines or lymphokines other than MCF, in the MCF assay, are shown in Table IV.

3) MCF Activity is Not Dependent Upon Natural Killer Cells (NK)

In order to remove human NK cells from whole human peripheral blood mononuclear cells, anti-Leu-11B was used (Becton Dickinson, Mountain View, Calif., USA) (Itch et al., *J. Immunol.*, 134:802, 1985). Human monocyte monolayers were treated with anti-Leu-11B and subjected to either activation with MCF for measurement of cytotoxicity, or staining with trypan blue for viability. Human monocyte monolayers treated with anti-Leu-11B plus complement and activated with MCF did not diminish MCF mediated cytolysis, nor was viability at the monocyte monolayers decreased when compared to control monolayers. Monocyte monolayers were activated with either crude MCF (23.8 U/ml) or MCF prepared by Matrex Gel Red A chromatography (83.3 U/ml). Cytotoxicity was measured using K562, HL60, L5178Y or TU5. Specific release of MCF was comparable with both NK-sensitive and NK-resistant (TU5 and L5178Y) cells. (Table V)

TABLE IV

Effect of other cytokines in the MCF assay

| Cytokine | U/ml | % specific lysis | MCF U/ml | Specific antisera treatment of MCF | | |
|---|---|---|---|---|---|---|
| IFN-α | 1000 | −8.9 ± 8.8 | 18.1 ± 2.6 | αIFN-αinput | Exp. 1 | Exp. 2 |
| | 100 | −2.1 ± 12.4 | | | % specific lysis | |
| | 10 | −5.4 ± 9.2 | | 0 U/ml | 54.6 ± 3.8 | 29.8 ± 5.4 |
| | 1 | 4.5 ± 3.0 | | 100 | 57.6 ± 5.0 | 35.8 ± 4.2 |
| | | | | αIFN-γ input U/ml | Native U/ml | N-terminus |
| IFN-γ | 1000 | 6.2 ± 4.4 | 40.0 ± 2.9 | 0 | 27 | 27 |
| | 100 | 3.4 ± 3.2 | | 25 | 28 | 39 |
| | 10 | −3.5 ± 1.1 | | 50 | 58 | 46 |
| | 1 | −2.2 ± 1.9 | | 100 | 20 | 40 |
| eIL1α | 10 | −0.7 ± 7.6 | 24.4 ± 6.5 | | | |
| | 1 | −3.6 ± 5.6 | | | | |
| | 0.1 | −4.1 ± 4.1 | | | | |
| rIL1β | 10 | −1.8 ± 9.6 | 24.4 ± 6.5 | | | |
| | 1 | −4.9 ± 4.6 | | | | |
| | 0.1 | −8.7 ± 2.8 | | | | |
| pIl1 (α + β) | 100 | −10.2 ± 4.0 | 18.1 ± 2.6 | | | |
| | 10 | −5.2 ± 2.7 | | | | |
| | 1 | −5.4 ± 7.9 | | | | |
| | 0.1 | −10.9 ± 3.3 | | | | |
| rIL2 | 1000 | 2.7 ± 6.2 | 20.0 ± 2.0 | | | |
| | 100 | −3.2 ± 3.5 | | | | |
| | 10 | −4.6 ± 4.3 | | | | |
| | 1 | −10.2 ± 17.7 | | | | |
| GM-CSF | 200 | −0.6 ± 4.9 | 20.0 ± 4.4 | | | |
| | 100 | 5.7 ± 3.1 | | | | |
| | 50 | −2.5 ± 15.9 | | | | |
| | | | | am-CSF input U/ml | MCF activity U/ml | |
| m-CSF | 1730 | −3.9 ± 4.7 | 50.0 ± 3.9 | 0 | 33.3 | |
| | 173 | 14.5 ± 4.6 | | 100 | 40.0 | |
| | 17.3 | 26.0 ± 6.5 | | 1000 | 50.0 | |

Various cytokines were added to the MCF bioassay. Specific antisera were added to MCF-containing supernatants to determine whether any MCF activity could be neutralized by antisera to other cytokines.

TABLE V

MCF-induced cytotoxicity against tumor targets

| Target | MCF (units/ml) |
|---|---|
| crude MCF: | |
| K562 | 23.8 ± 9.1 |
| HL-60 | 23.5 ± 1.5 |
| partially purified MCF: | |
| K562 | 83.3 ± 12.3 |
| L5178Y | 78.4 ± 8.4 |
| TU5 | 100.5 ± 26.8 |

Monocyte monolayers were activated with either crude MCF or MCF prepared over Matrex Gel Red A for 24 h before the addition of targets.
Units were calculated as the reciprocal of the dilution giving 20% specific lysis.
These are the results of 3 experiments run in quadruplicate.

TNF could not be demonstrated in supernatants collected from human monocytes incubated with 20 U/ml MCF for 20 h, washed and incubated for 24 h (dilution of 1:10). However, IL 1 was present at concentrations of up to 100 U/ml in MCF-activated monocyte supernatant.

C. Response of MCF to Enzyme Treatment

In order to treat MCF supernatants with enzymes, 10 ml of the supernatant (28.5 units/ml) were treated with 1 mg/ml trypsin at pH 7.4, 1 mg/ml chymotrypsin at pH 7.4, 0.5 mg/ml DNase at pH 7.4, or 40 units/ml RNase at pH 5 for 1 hour at 25° C. The result of treating MCF with chymotrypsin was that there was a reduction in the biological activity of MCF by 54.4%. Trypsin, RNAse and DNAse had no significant effect. The experiments were repeated using insolubilized enzymes to minimize the possibility that enzymes could be carried over into the bioassay and could explain the results. However, the results were entirely comparable to those using soluble enzymes. Chymotrypsin reduced activity from 28.5 U/ml to 12.5 units, whereas trypsin RNAse and DNAse treatment showed no significant differences after one hour of treatment, as measured by bioassay for MCF and determined by students T test.

D. Effects of Tunicamycin and Other Agents on MCF

Urea treatment was accomplished by adding 3 grams of solid urea to 10 ml MCF (28.5 U/ml) (5M urea final). Extraction of MCF with butanol-diisopropyl ether was performed. FtF3 cells were cultured with 0, 1, 2.5 or 5.0 ug/ml tunicamycin. Urea decreased biological activity in the MCF containing supernatants by 35.7%. MCF supernatants were extracted with butanol-diisopropyl ether; the aqueous phase contained 36.7% less MCF than the control preparation. Biosynthesis in the presence of either 2-mercaptoethanol or tunicamycin resulted in no significant change in biological activity of MCF.

E. Effects of Metabolic Inhibitors on MCF

FtF3 cells at a concentration of $1\times10^6$/ml in RPMI 1640/10% FCS were incubated 4 hours with either actinomycin D, cycloheximide, or puromycin (all at 0 to 100 ug/ml, Sigma). Tests for viability after treatment were performed by trypan blue exclusion and supernatants were collected by centrifugation. In a second set of experiments FtF3 cells at the same concentration but using 0.1% human serum were incubated for 5 hours with either cycloheximide or puromycin. Uptake experiments were performed by adjusting FtF3 cells to $1\times10^6$ /ml in media after treatment with inhibitor, and adding either 5,6-$^3$H-uridine (ICN Radiochemicals, Irvine, Calif., USA, 49,Ci/mmol) to actinomycin D treated cells or $^3$H L-amino acid mixture (25.5 mci/mg) to cycloheximide-treated cells at 1 uCi to $1\times10^5$ cells. Cells were subsequently lysed and counted by liquid scintillation.

Figure 2:
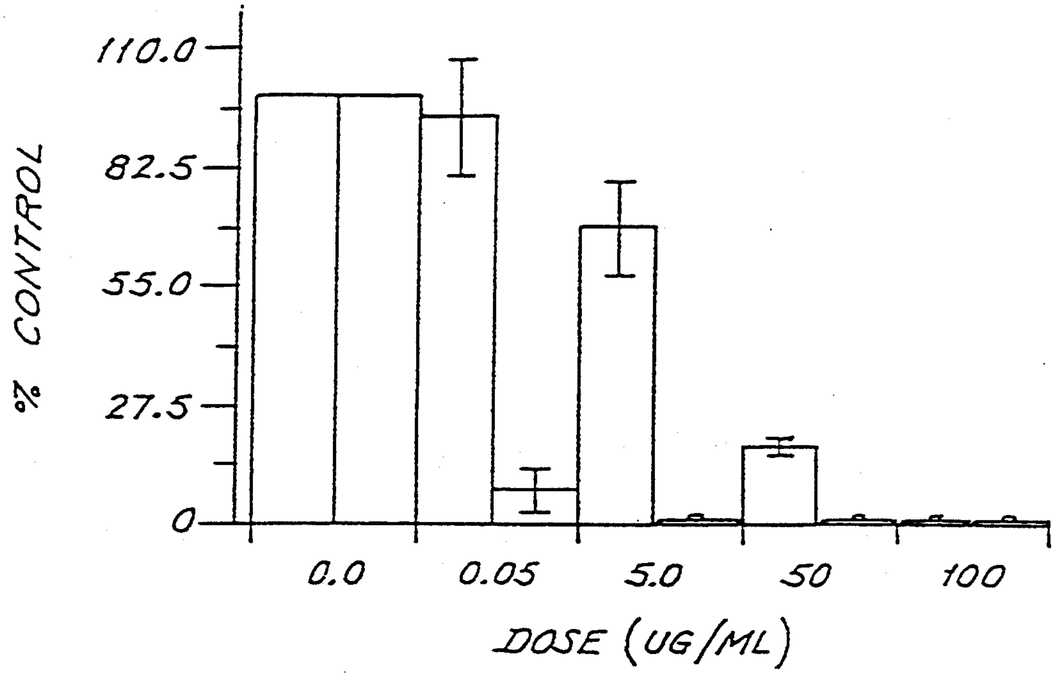
FIG. 2. FtF3 cells were incubated 4 h with various doses of actinomycin D. Cells were washed and stimulated with PHA for 24 h before harvesting supernatants by centrifugation, extensive dialysis, and bioassay.( ) One set of each dose of inhibitor-treated cells was labelled with $^3$H-uridine, stimulated, lysed and harvested 24 h later, and counted by liquid scintillation.(□) Viability of FtF3 at 24 h was greater than 80% at all doses tested.
Figure 3:
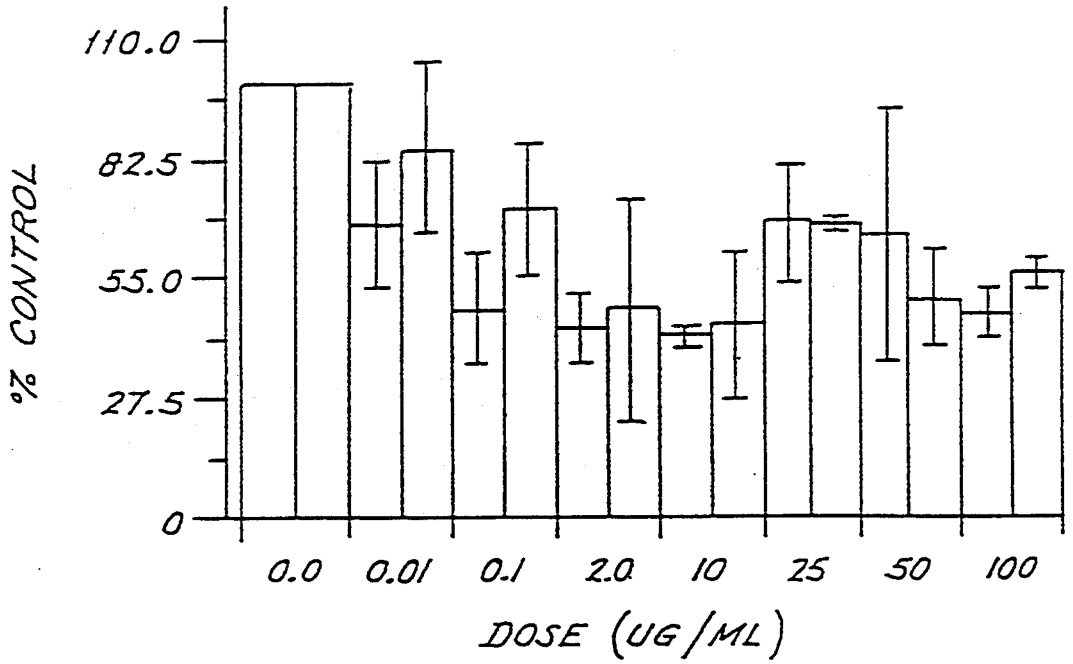
FIG. 3. FtF3 cells were incubated 4 h with various doses of cycloheximide. Cells were washed and stimulated with PHA for 24 h before harvesting supernatants by centrifugation, extensive dialysis, and bioassay.( ) One set of each dose of inhibitor-treated cells was labelled with 3 H-amino acids, stimulated, TCA-precipitated 24 h later, and counted by liquid scintillation.(□) Viability of FtF3 at 24 h was greater than 80% at all doses tested.
Figure 4:
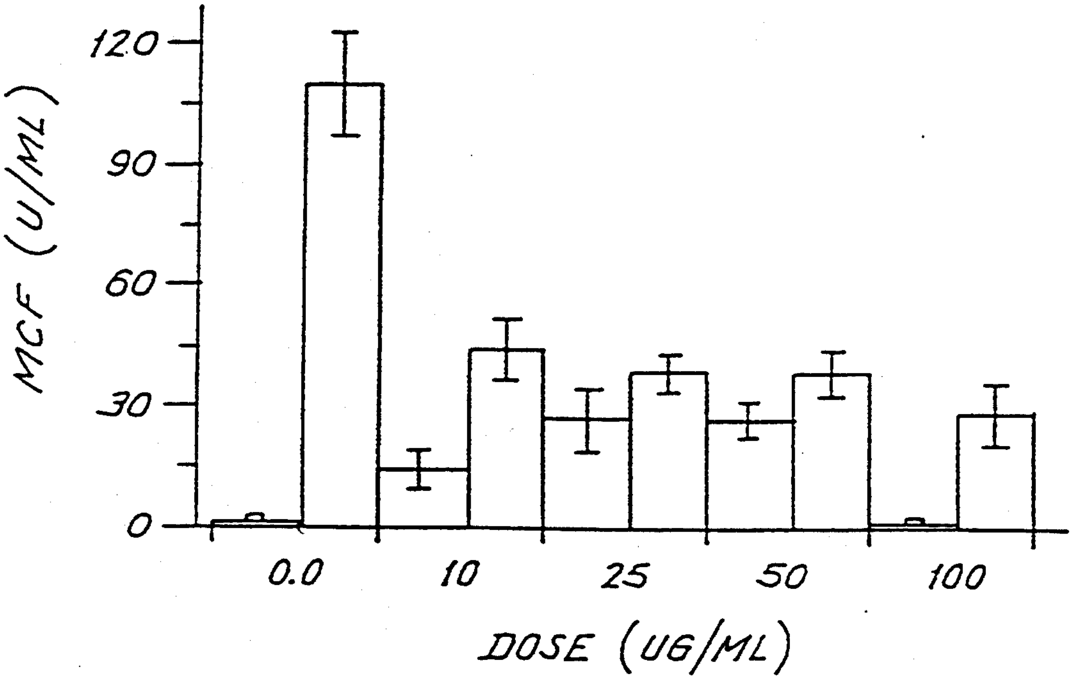
FIG. 4. FtF3 cells were incubated 4 h with various doses of puromycin. Cells were washed and resuspended either with ( ) or without (□) PHA, and incubated 24 h before harvesting supernatants by centrifugation, extensive dialysis, and bioassay. Viability of FtF3 at 24 h was greater than 80% at all doses tested.

When MCF was grown in the presence of the metabolic inhibitors, actinomycin D totally suppressed production of MCF in a dose-dependent manner accompanied by a corresponding fall in $^3$H-uridine uptake (FIG. 2). Cycloheximide suppressed but did not abolish MCF production (FIG. 3). At intermediate doses (25 and 50 ug/ml) some escape from suppression was noted. Puromycin, like cycloheximide, suppressed but did not totally abolish MCF production under these conditions (FIG. 4). A corresponding pattern was observed using tritiated amino acids and examining the pattern of incorporation in TCA insoluble material.

Actinomycin D had no effect, and cycloheximide had only a slight stimulatory effect, on MCF production of nonstimulated (non-PHA treated) cells. Puromycin at doses of 10–50 ug/ml appeared to stimulate production of MCF by FtF3 cells not activated by lectin. Cycloheximide and puromycin therefore provide reversible inhibition. When inhibitor was present for the entire incubation period, lectin-induced MCF production is not suppressed by cycloheximide but puromycin was suppressive in a dose-dependent manner.

F. MCF Behavior in other Bioassays

The biological activity of MCF was checked in other bioassays to probe the issue of multiple biological activities. Supernatants from FtF3 containing 25 U/ml of MCF activity were substituted for IL 1 and IL 2 in their respective bioassays. MCF demonstrated no IL 1 or IL 2 activity. MCF had no TNF, M-CSF, or IFN-like antiviral biological activity when compared to RTNF, purified human m-CSF, IFN-gamma or alpha/beta respectively.

G. Physicochemical Characterization of MCF 1) pH Stability pH stability of MCF was compared to IFN-gamma by dialyzing 40 U MCF or 100 U IFN-gamma in Spectropor tubing (molecular weight cutoff of $5\times10^3$ Daltons) against 0.1M glycine-HCl, pH 2.0, 0.1M TRIS-HCl, pH 5.0, 0.15M PBS, pH 7.4, 0.15M PBS, pH 8.0, or O.lM TRIS, pH 10.0 for 4 hrs at 25° C. The samples were then dialyzed against Dulbecco's PBS, pH 7.4, to restore neutrality prior to bioassay. IFN-gamma was found to be totally inactivated at pH 2. However, as demonstrated by Table VI, MCF was found to be stable at pH 2. However, partial inactivation of MCF has consistently been noted at pH 8.0.

TABLE VI pH Stability of MCF

| pH | % Specific Lysis |
|---|---|
| 2 | 41.7 ± 8.6 |
| 5 | 41.1 ± 6.4 |
| 7.4 | 36.8 ± 3.2 |
| 8 | 19.6 ± 4.6 |
| 10 | 45.4 ± 5.4 |

2) Heat Stability of MCF

To test heat stability of MCF relative to IFN-gamma, 40 units of MCF and 100 U IFN-gamma in 1 ml RPMI 1640/1% FCS were heated for 2 hrs in a constant temperature bath to study heat denaturization. As demonstrated by Table VII, MCF was stable at temperatures up 60° C., but was totally inactivated at 100° C. IFN-gamma was not stable at temperatures higher than 4° C. for periods of 2 hrs or longer.

TABLE VII

Heat Stability of MCF

| Temperature | % Specific Lysis |
|---|---|
| 4° | 53.3 ± 4.3 |
| 37° | 48.6 ± 4.9 |
| 60° | 48.0 ± 3.4 |
| 100° | 0.0 |

7. Preliminary Purification of MCF

A. Gel Filtration of MCF

Gel filtration experiments were performed to give an indication of approximate molecular weight. 180 ml of MCF from PHA stimulated FtF3 supernatant ($7.2\times10^3$ U MCF) was concentrated 20-fold by pressure dialysis over an Anicon YM-10 membrane, applied to a $2.5\times60$ cm. column of Bio-Gel P100, equilibrated with PBS and eluted at a flow rate of 1.5 ml/min. 7.5 ml fractions were collected and were assayed undiluted, ½, and 1/5 for MCF activity. The column was calibrated with aldolase (158K), ovalbumin (45K), chymotrypsin (25K), and ribonuclease A (13.7K) (Pharmacia).

Figure 5:
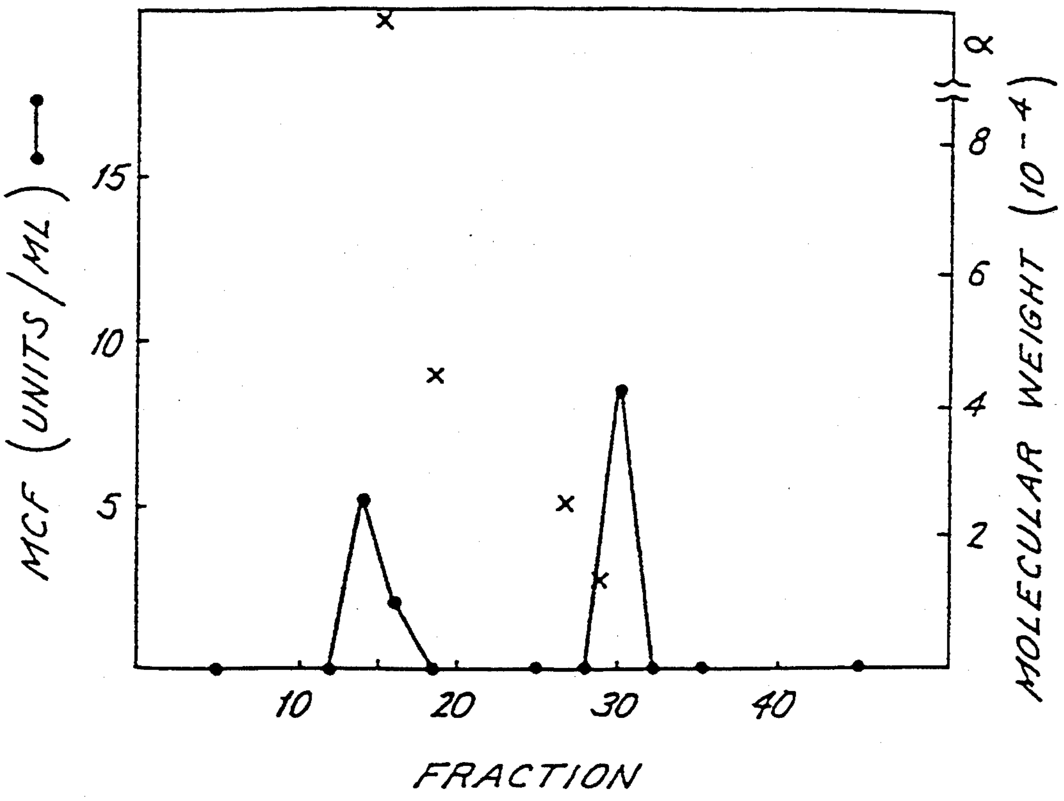
FIG. 5. $7.2\times10^3$ U of MCF in 28 ml was applied to a $2.5\times60$ cm column of Bio-Gel P 100 equilibrated with PBS pH 7.4. The column was eluted at 1.6 ml/min and 7.5 ml fractions were collected. (°—°) F units/ml; (x) represent the molecular weight standards: ribonuclease A 13,700, chymotrypsinogen A 25,000, ovalbumin 45,000, and aldolase 158,000. Molecular weight determinations were calculated using Curvfit program (Interactive Microware, Inc. State College, Pa.) on an Apple II+ system.

The data in FIG. 5 demonstrated that two peaks of biological activity were obtained. The first peak co-eluted with the major protein present, bovine serum albumin (from the fetal calf serum present in the culture media). The second peak of monocyte cytotoxicity inducing activity eluted in a region with an apparent molecular weight of approximately 11,500 Daltons.

B. Precipitation with Ammonium Sulfate

Initially, ammonium sulfate precipitation was attempted as a method for purification and concentration. MCF appeared to precipitate in the 30–50% range but resulted in greater than an 85% loss in biological activity. Therefore, ammonium sulfate precipitation was not pursued further as a means for purification.

C. Binding of MCF to Matrex Gel Resins

Two ml of each of the Matrex Gel Resins (Amicon) was washed with 5M Urea and then washed with 20 ml PBS in 1.5M NaCl, pH 7.4. Four ml of FtF3 supernatant (160 U MCF in RPMI 1640, 1%FCS) was passed twice over each of the Matrex Gel Resins (Blue A, Red A, Orange A, Green A, and Blue B), washed with 2 volumes of starting buffer, and eluted stepwise with 1 volume each 0.5M NaCl. 1.OM NaCl, and 2 volumes 1.OM NaCl/ 50% ethylene glycol. The starting material, wash, and each fraction was then dialyzed at 4° C. for 24 hrs (Spectrapor tubing, $5\times10^3$ D molecular weight cut off) against 3 changes of PBS, pH 7.4, and then 4 hrs against distilled $H_2O$. The samples were placed in a glass tray and covered with Sephadex G-10 to reduce volume to approximately 1 ml. Each sample was then assayed for units MCF activity.

Figure 6:
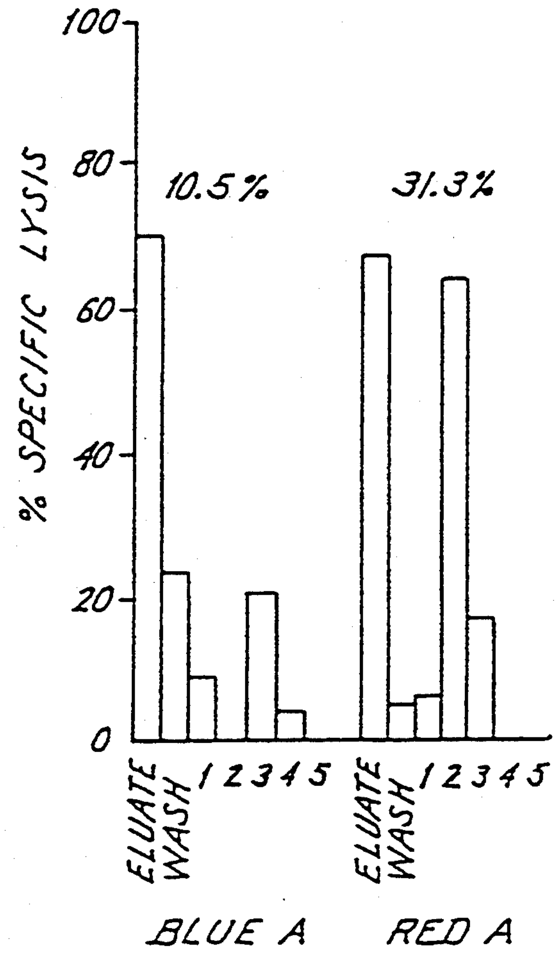
FIG. 6. 4 ml FtF3 supernatant was passed twice over 2 ml resin bed volume and eluted with a salt gradient. 10.5 and 31.3% activity could be eluted with 1M NaCl on Blue A and Red A, respectively. Biological activity was not recovered using Orange A, Green A, or Blue B.

MCF was bound and could not be eluted from Matrex Gels Orange A, Green A, and Blue B. However as summarized in FIG. 6, MCF bound to both Blue A, and Red A. Red A bound 31.3% of the starting material and eluted with 1.OM NaCl. Blue A bound only 10.5% of the starting and was not studied further.

8. Further Purification of MCF & Constituent Polypeptides

A. Matrex Gel Red A Chromatography

Ft. F3 serum-free supernatant was diluted 1:1 with distilled $H_2O$ before application to a Matrex Gel Red A column (50×2.5 cm), equilibrated with 20 mM phosphate-buffered saline (PBS)/0.15N NaCl, pH 7.4. The column was eluted with a 0–1N NaCl step gradient. Fractions were tested for biological activity, and protein was quantitated by comparison with ovalbumin silver-stained standards in a 15% SDS-PAGE gel. Fractions containing biological activity were pooled and dialyzed against distilled $H_2O$ until the conductivity fell below that of the following starting buffer. This purification step resulted in a recovery of 90% of the biological activity in less than 10% of the starting protein.

B. Ion-Exchange Chromatography

The dialyzed fractions from the Matrex Gel Red A chromatography step were applied to a 1.5- ×25-cm diethylaminoethyl (DEAE) cellulose column equilibrated with 0.02M Tris, pH 8.4, and eluted with a 0–0.5 N Nacl/0.02M Tris gradient at a flow rate of 2 ml/min. Biological activity and protein were measured in the same manner as for the dye ligand column. The peak biologically active fractions, discarding the trailing fractions, were pooled, dialyzed against distilled $H_2O$, and lyophilized to dryness.

Figure 7:
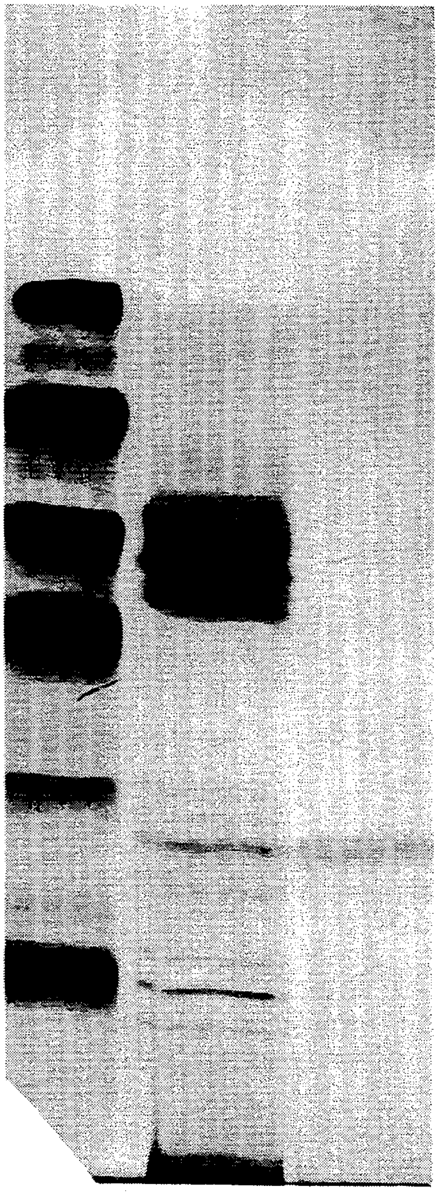
FIG. 7. SDS-PAGE (15%) of P29 from DEAE cellulose. Lane 1, peak of DEAE cellulose biological activity; lane 2, crude supernatant from Ft. F3 concentrated 100× by lyophilization; and lane 3, BRL low molecular weight standards.

Only a single 29kD protein band prove these pooled fractions can be visualized on a silver-strained gel (FIG. 7). However, when companion gels were cut into 1 cm segments and the proteins were eluted from the gel, biological activity was found to be present in fractions corresponding to molecular weights of both 29kD and 14.7kD.

These DEAE-recovered fractions were used as the starting materials for the further purification of the individual polypeptides P29 and P14.7

C. Polyacrylamide Gel Electrophoresis (SDS-PAGE) to Prepare MCF P29

A sample of the MCF-containing lyophilized material obtained following DEAE chromatography was subjected to preparative SDS PAGE. The sample was mixed with sample preparation buffer (0.0625 ml TRIS-HCl, 2% SDS, 5% 2ME, 10% sucrose, and 0.002% bromphenol blue), heated 3 min at 100° C. and centrifuged at high speed (1 min in an Adams microfuge). 100 μl aliquots were loaded into each of 4 lanes of a 2 mm thick preparative SDS slab gel (BRL vertical gel apparatus, Gaithersburg, Md.) using a 15% polyacrylamide gel, prepared according to Laemmli (*Nature,* 227:680, 1970), and run at 90 V through the stacking gel and 200 V through the running gel. The gel was cut into 1 cm slices, crushed, eluted with 2 washes of 5 ml of PBS/0.1% SDS pH 7.4, for 12 hours at 4° C., and the biological activity of the eluted material was determined. Pharmacia low molecular weight standards prepared in the same buffer and run in companion lanes were used to determine molecular weight: ovalbumin (43kD), α-chymotrypsinogen (25.7kD), oval-a-lacto-globulin (18.4kD), lysozyme (14.3kD), bovine trypsin inhibitor (6.2kD), and insulin A or B chain, (2.3kD and 3.4kD). A companion gel was divided and stained with 1) Coomasie Brilliant Blue and 2) by a silver nitrate method (Oakley et al., *Anal. Biochem.,* 105:361, 1980).

Preparative SDS PAGE and elution in this manner was found to be particularly suitable for the preparation of P29 polypeptide for further analysis. However, as mentioned above, elution of P29 preparative PAGE gels in the region of 14.7 kd demonstrated that MCF biological activity was present despite the inability to visualize protein employing either silver staining of the primary gel or colloidal gold (Aurodye) staining of the resultant Western blots. This tends to indicate that P14.7 may not be present in a high enough concentration to allow detection, perhaps partly because some loss of protein occurs during the blotting and washing procedures themselves. Alternatively blotting to nitrocellulose may have altered its antigenic reactivity during the processes of denaturation and rebinding to a foreign surface.

D. Hydrophobic Chromatography to Prepare MCF P14.7

A further method was developed to yield a reliable source of pure P14.7. A sample of the MCF-containing lyophilized material obtained following DEAE chromatography was resuspended in 2 ml 0.01M phosphate buffer, pH 6.8, and brought to 8M ammonium sulfate. This sample was then applied to a 0.5- ×12-cm octyl sepharose column equilibrated with 0.01M phosphate buffer, pH 6.8, and 8M ammonium sulfate. Protein was eluted with a declining gradient of ammonium sulfate (8-0M) and an increasing SDS (0–0.5%) gradient. Column fractions were analyzed by SDS-PAGE.

Figure 8:
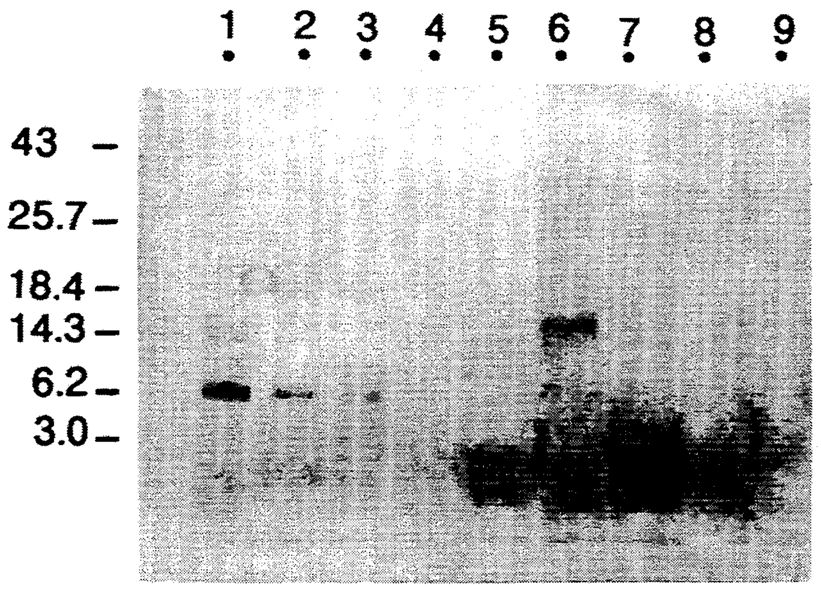
FIG. 8. Gel electrophoresis of fractions from the octyl sepharose column. Lanes 1–3 are serial dilutions of low molecular weight standards. Lanes 4, 5, 6, 8, and 9, are fractions obtained at approximately equal intervals from the octyl sephasose column. Lane 6 contains the peak of the biological activity. Lane 7 is the control starting material.

Hydrophobic chromatography in this manner generated two peaks, one of which was not retained by the resin and a second which bound tightly. Gel analysis of the second peak revealed a single protein band at 14.7 kd (FIG. 8). Nearly identical results were obtained using a Lichrosorb RP8 column with an acetonitrile/-pyridine mobile phase.

Characterization and Analysis of MCF Polypeptides P29 & P14.7

A. Relationship of P29 and P14.7

In order to determine if the 14.7-kd species could be derived from the 29-kd species, three types of experiments were performed. Firstly, P29 was eluted from 15% PAGE gel and subjected to treatment with endoglycosidase F as follows. Five hundred micrograms of protein in 0.1 ml-0.05 N NaCl, 1% SDS, pH 6.8 incubation buffer, was denatured at 100° C. for 3 min. The SDS was precipitated with 1.0% nonionic detergent NP-40, and the reaction carried out by the addition of 5 and 10 U of endoglycosidase F (Boehringer Mannheim) followed by an overnight incubation at 37° C. It was found that P14.7 could not be generated from P29 by simple deglycosylation using endoglycosidase F treatment.

Secondly, P29 was subjected to performic acid oxidation. DEAE-prepared P29 protein was dissolved in 250μl cold performic acid (100 μl 30% $H_2O_2$ plus 900μl concentrated formic acid incubated 1 h at room temperature) and held 4 h at 4° C. This was diluted to 3.0 ml with distilled $H_2O_2$ frozen in dry ice and ethanol, and lyophilized. Products from both procedures were recovered by repetitive lyophilization and analyzed by SDS-PAGE. Performic acid treatment in this manner did not result in regeneration of P147 from P29. Neither did treatment with excess (40×) β-mercaptoethanol.

Lastly, P29 and P14.7 were compared immunologically. Antisera to P29 and P14.7 were prepared as follows. Two New Zealand white rabbits were immunized with 600 μg of purified P29 MCF in complete Freund's adjuvant at multiple sites. Rabbits were boosted at 2-week intervals with 100 μg P29 MCF in incomplete Freund's adjuvant. A third rabbit was immunized in the same manner with purified P14.7 MCF prepared from octyl sepharose. Specificity of both antisera was tested by dot immuno-blotting using human serum, purified human IL-1, recombinant human IL-1α and IL-1β (Centikor), purified human tumor necrosis factor alpha (TNF-α; gift of Dr. Paul Massaferro, Bissendorf Peptides, Dallas, Tex.), purified human CSF-1 (gift of Dr. Richard Shadduck, University of Pittsburgh), recombinant GM-CSF (gift of Dr. Saroj Vadhan-raj, Department of Clinical Immunology, M.D. Anderson Hospital), and purified human IFN-α, IFN-β, and IFN-γ (gifts of Dr. Samuel Barron, University of Texas Medical Branch, Galveston, Tex.).

On testing the specificities of the antisera raised to P29 and P14.7, neither was found to react with whole human serum, IL-1α, IL-1β, TNF-α, CSF-1, IFN-α, IFN-β, or IFN-γ. To compare the P27 and P14.7 polypeptides directly, a sample (100 ml) of crude Ft. F3 supernatant was dialyzed, lyophilized, electrophoresed in two dimensions (as described by O'Farrell, *J. Biol. Chem.*, 250:4007, 1975), and subjected to immunoblotting.

The immunoblots were developed according to the method of Bennett and Yeoman (*J. Immunol. Methods*, 61:201, 1983) using alkaline phosphatase-labeled goat anti-rabbit IgG (Kirkegaard and Perry, Bethesda, Md.) as a secondary antibody. It was found that antiserum to P29 recognized only P29 in such immunoblots of crude hybridoma supernatant 2D gels.

B. Amino Acid Composition

P29 prepared by dye ligand and ion exchange chromatography and SDS gel electrophoresis in one dimension, was cut and eluted from a single 15% gel, lyophilized, and re-electrophoresed for 2D analysis. Protein blotting of the second dimension as well as silver staining of the primary gel revealed a major spot at 29 kd having an isoelectric point of 4.2. This spot was cut out of the second dimension, eluted, lyophilized to dryness, and subjected to amino acid composition analysis.

Amino acid analysis was carried out on 250 pmoles of P29 utilizing overnight acid hydrolysis followed by analysis on an LKB model 4151 alpha plus amino acid analyzer. Peaks were compared to authentic standards (LKB) (Levy et al., *PNAS*, 76:6186, 1981). The results of the amino acid composition are summarized below:

TABLE VIII

Amino Acid Composition Analysis of P29 MCF

| | Mole percent | | Mole percent |
|---|---|---|---|
| Asp | 8.06 | Ile | 4.06 |
| Thr | 3.89 | Leu | 7.39 |
| Ser | 9.05 | NorL | — |
| Gln | 12.40 | Tyr | 3.06 |
| Gly | 20.06 | Phe | 3.25 |
| Ala | 7.51 | His | 2.83 |
| Cys | — | Lys | 5.72 |
| Val | 5.08 | Arg | 3.94 |
| Met | 0.99 | Pro | 2.72 |

380 moles of P14.7, purified by hydrophobic chromatography, was similarly subjected to amino acid analysis giving the following results:

TABLE IX

Amino Acid Composition Analysis of P14.7 MCF

| | Mole percent | | Mole percent |
|---|---|---|---|
| Asp | 11.2 | Ile | 5.4 |
| Thr | 4.8 | Leu | 7.6 |
| Ser | 5.1 | NorL | — |
| Gln | 9.2 | Tyr | 2.2 |
| Gly | 19.25 | Phe | 3.8 |
| Ala | 9.2 | His | 1.2 |
| Cys | — | Lys | 5.1 |
| Val | 6.8 | Arg | 4.0 |
| Met | 1.1 | Pro | 3.9 |

It can be seen that the amino acid composition analyses of both species are similar but not identical. Both proteins are rich in glycine. However, this occurs as a contaminant in such analysis and these results should therefore be confirmed by primary sequencing.

C. N-terminal Sequence Analysis

The purified MCF P29 and P14.7 polypeptides were prepared, as described above, and subjected to automated Edman degradation in Beckman Model 890 Sequenator. The N-terminus of P29, as determined from three separate preparations, reads in the three-letter amino acid code—Gly Ala Ala Val Leu Glu Asp Ser Gln, whereas that of P14.7 is blocked (results are from determinations using 250, 320, and 380 nmol of each protein).

The N-terminal sequence of P29 was compared with those in the PIR (Protein Identification Resource), National Institute of General Medical Sciences, and the EMBL Data Banks and was found to be unique.

To summarize, the data presented above suggest that the MCF P29 and P14.7 polypeptides may be distinct, but related, proteins important in the induction of monocyte cytotoxicity. Furthermore, an N-terminal analysis of P29 reveals it to be a previously undescribed cytokine.

10. MCF Activity of Synthetic Peptides

A 9-mer synthetic peptide corresponding to the authentic N-terminal amino acid sequence of MCF P29 was prepared using a Water's Mode; 438 Synthesizer. The peptides were cleaved from the resin and purified by hydrophobic HPLC over an Aqua Pore C4 column using a TFA/acetonitrile gradient. Coupling was monitored by the Ninhydrin method (Kent, *The chemical synthesis of peptides and proteins annual review of biochemical chemistry*, 15:951, 1988). The peptide was purified by rechromatographing on a C4 reverse phase column and repeated lyophilization. The fidelity of synthesis was determined by N-terminal sequence analysis using an Applied Biosystems Model 477A sequencer. This peptide, having the sequence Gly Ala Ala Val Leu Glu Asp Ser Gln (seq id no:1), was termed MJ-2.

Figure 9:
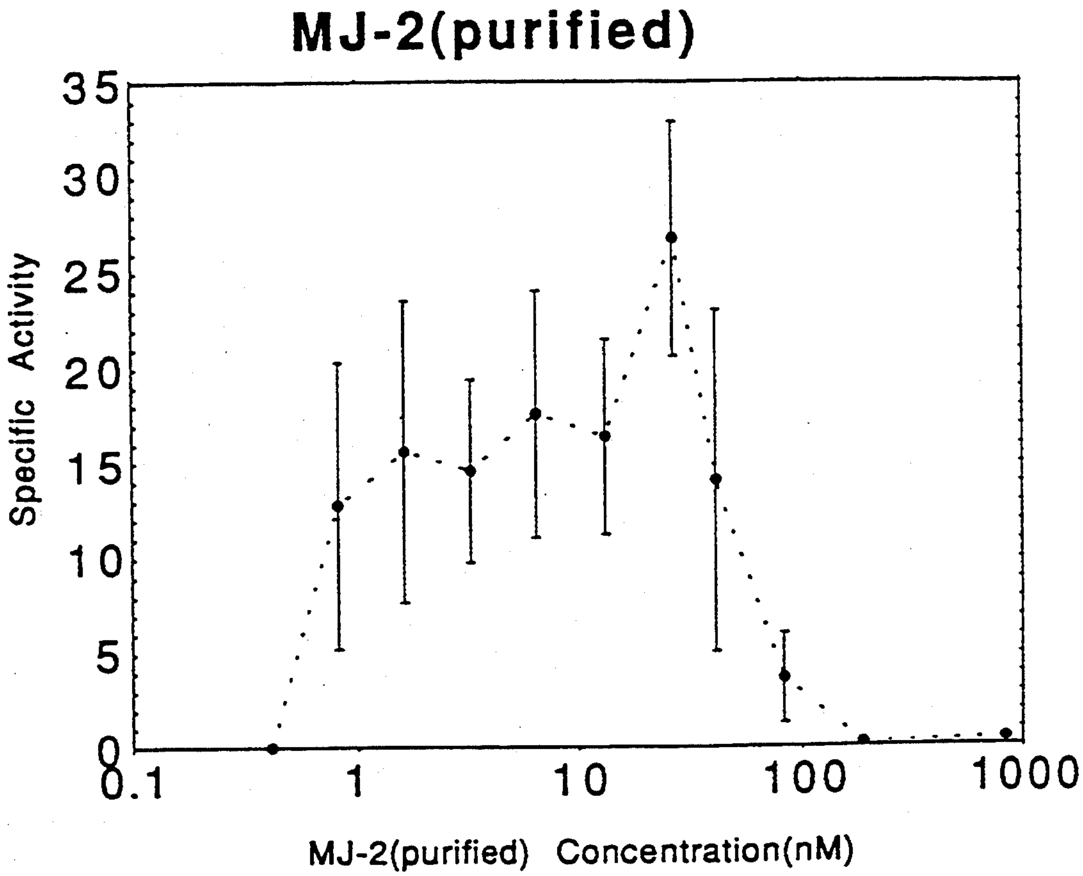
FIG. 9. Dose response curve of the activity of the purified peptide Gly Ala Ala Val Leu Glu Asp Ser Gln (Seq id no:1), termed MJ-2, representing the native 9 N-terminal amino acids of P29. The activity represents specific lysis of the human tumor target K562 by activated human peripheral blood monocytes, as described herein. The peptide was purified by rechromatographing on a C4 reverse phase column and repeated lyophilization, the concentration of the purified peptide is given in nanomoles. The bars represent the standard deviation from the mean, which is the result of using eight different human donors.

The potential monocyte cytotoxicity inducing activity of the purified MJ-2 peptide was tested, as before, using assays based upon the specific lysis of the human tumor target K562 by activated human peripheral blood monocytes. The purified MJ-2 peptide was found to be capable of activating human blood monocytes for cytotoxicity at a concentration of approximately $10^{-9}$M (FIG. 9). This level of activity is particularly noteworthy as this peptide, of only 9 amino acids, exhibits the same high level activity as the intact protein of 29kD. Furthermore, the peptide was found to be capable of activating the monocytes obtained from eight different human donors. The standard deviation between assays using monocytes from different human subjects was found to be relatively low in comparison to the high variability which is usually observed in assays of human immune function.

Further truncated or substituted synthetic peptides were also synthesized, purified, and analyzed for monocyte cytotoxicity inducing activity.

Figure 10:
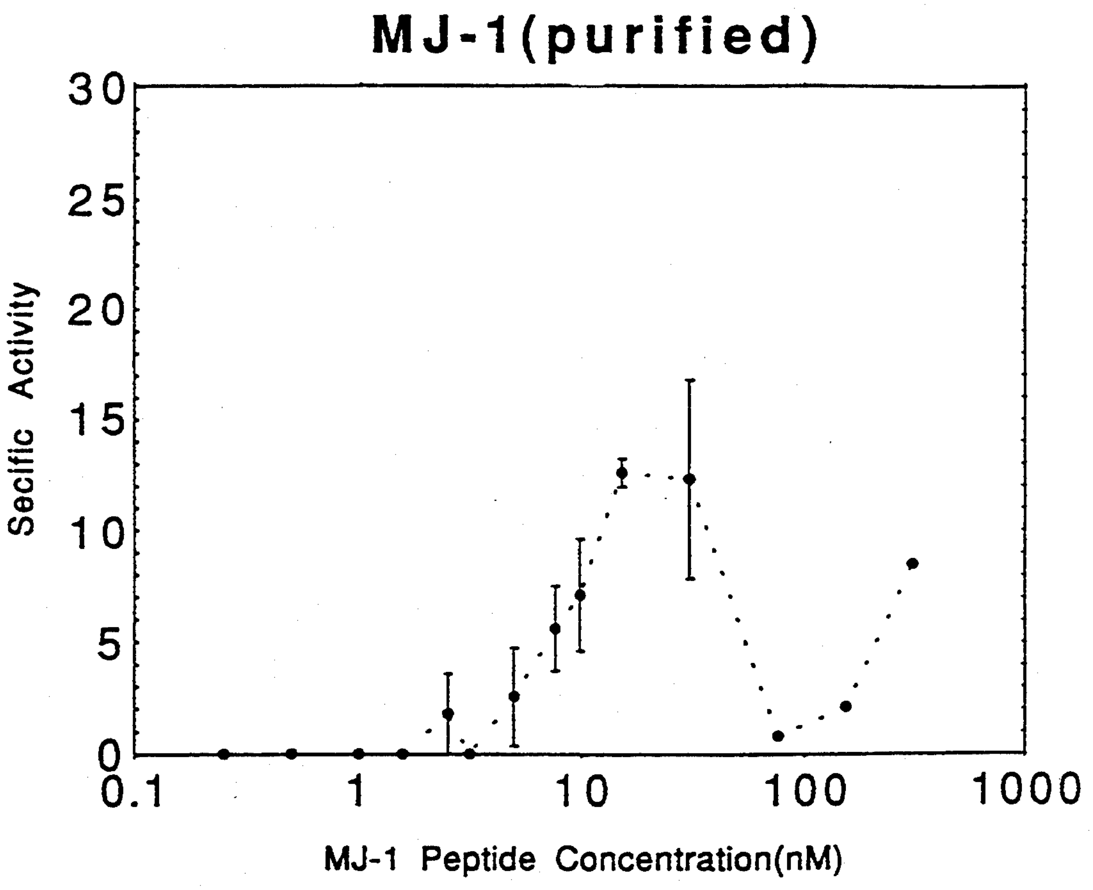
FIG. 10. Dose response curve of the activity of the purified peptide Gly Ala Ala Val Leu Glu <u>Asn</u> Ser Gln (Seq id no:2), termed MJ-1, containing a aspartic acid at position 7 instead of asparagine. The study was performed as described for FIG. 9.

A purified peptide termed MJ-1, having the sequence Gly Ala Ala Val Leu Glu Asn Ser Gln (seq id no:2) i.e., containing an asparagine at position 7 instead of an aspartic acid residue, was also found to be capable of inducing human monocyte cytotoxicity. When tested in an identical manner to MJ-2 in parallel assays using cells from the same human donors, the activity of the substituted peptide, MJ-1, was determined to be $10^{-6}$M (FIG. 10). This data indicates that the substitution of this particular single amino acid residue results in an approximate 3 log fold decrease in the biological activity of the peptide.

Figure 11:
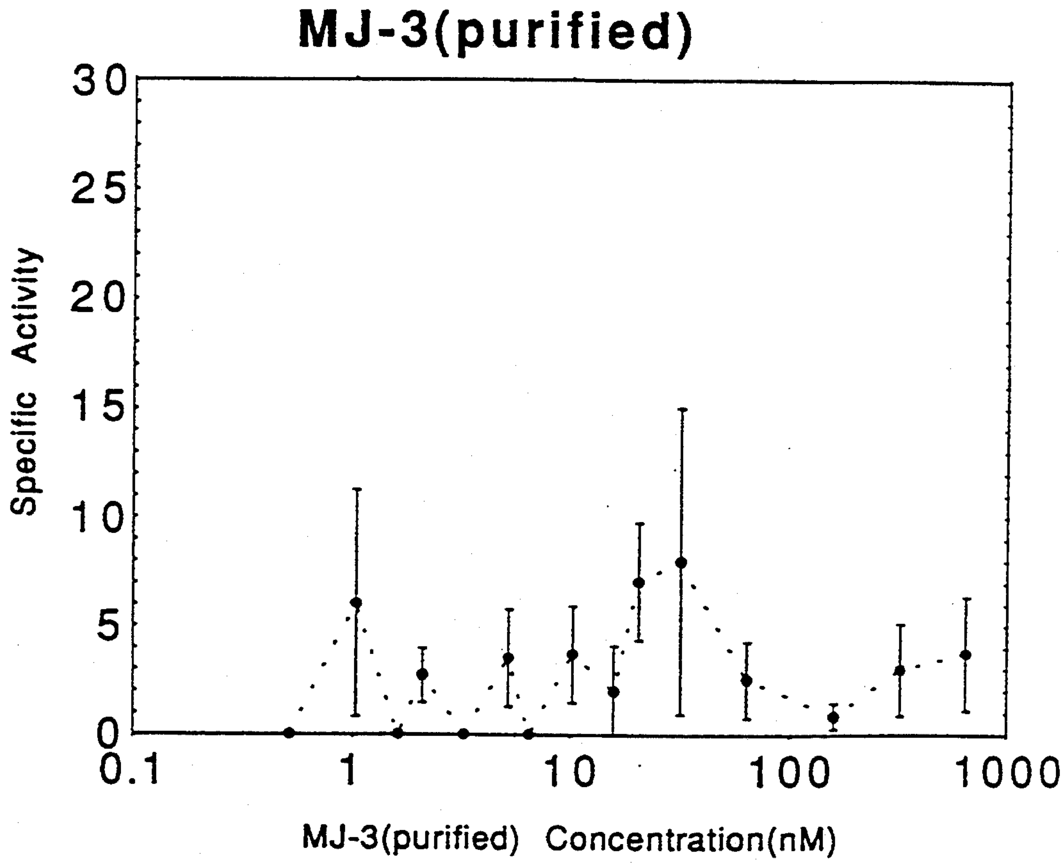
FIG. 11. Dose response curve of the activity of the purified peptide Gly Ala Ala Val Leu, termed MJ-3, representing the native 5 N-terminal amino acids of P29. The study was performed as described for FIG. 9. This activity was not determined to be above the background for the assay.

A truncated five-mer peptide, MJ3, having the sequence Gly Ala Ala Val Leu, did not reliably exhibit biological activity when tested in parallel assays (FIG. 11). No dose response could be obtained, although in one experiment 25% specific release of label was observed at an input of $10^2$ mg of protein. However, the 5-mer peptide MJ-5 with the sequence Leu Glu Asp Ser Gln (seq id no:3) was critical for biological activity.

11. Treatment Protocols

Due to precautions which are necessarily attendant to every new pharmaceutical, due both to consideration of patient safety and federal new drug regulations, the MCF and MCF peptides of the present invention have not been tested as yet in a clinical setting in human subjects. However, the in vitro activity of MCF in stimulating monocytes to kill tumor cells, along with the recent clinical success of interleukin II, is believed to demonstrate the utility of the present invention in this regard. The following embodiments are therefore prophetic and represent the best mode contemplated by the present inventor of carrying out the practice of the invention in various clinical settings.

A. Antitumor Therapy

1) Direct Infusion

It is believed that MCF or MCF-derived peptides or synthetic peptides will prove to be useful in the treatment of various tumors, and in particular, tumors of the blood forming organs such as leukemias, or solid tumors which have been described as infiltrated by macrophages, by way of direct intravenous infusion of pharmaceutical compositions which include MCF. Such compositions would include effective doses of either MCF alone, or in combination with other therapeutic agents such as interleukin II, interferon, tumor necrosis factor or cytoxan. Interleukin II may be obtained as disclosed by numerous U.S. patents, including for example, U.S. Pat. No. 4,407,945 and 4,401,756, incorporated herein by reference. Cytoxan (cyclophosphamide) is a commercially available antineoplastic agent. Interferon is also commercially available as disclosed here@in, and its clinical use has been reviewed and described in detail in numerous publications, including, for example, in Goldstein et al., *Can. Res.*, 46:4325–4329, 1986, incorporated herein by reference. Moreover, Goldstein discloses in detail the suggested and reported dose regimens for interferon antitumor therapy. Preparation of Tumor Necrosis Factor and its use is known in the art as exemplified by U.S. Pat. Nos. 4,457,916; 4,529,594; and 4,447,355 and as further disclosed by Carswell et al., *Proc. Natl. Acad. Sci, USA,* 72:3666, 1975; Ruff et al., *J. Immunol.,* 125:1671, 1980; Matthews et al., *Br. J.* 46(9):4357, 1980, all of the foregoing references being incorporated by reference. Therefore, it is considered that use and dosages of MCF treatment, alone or in combination with these agents, is well within the skill of the art in light of the present specification.

MCF, MCF-derived peptides or synthetic peptides could be given daily by continuous infusion or given on alternative days with interleukin-2 or interferon being given on the other day. Such a treatment would be possible since the cytotoxic effect of MCF seems to last for about approximately 24 hours. Alternatively a large initial dose of Cytoxan could be given which should deplete suppressor T-lymphocytes followed by continuous infusion of MCF. Doses of MCF would of course have to be determined by experimental methods which are well known to skilled immunologists. However, dosages will likely be at least an order of magnitude lower than dosages of interferon gamma. Interferons are usually given as an IM dose of 3 million units thrice weekly although one would have to take into account whether total body water is being saturated. With a new agent of any type one would have to initiate a phase I trial first to establish levels at which unacceptable toxicity is reached.

2) Adoptive Immunotherapy

Adoptive immunotherapy is a new approach to treating metastatic cancer in which immune cells with antitumor reactivity are transferred to the tumor-bearing patient. Much of this work has been pioneered by Dr. Steven Rosenberg and is discussed in more detail in Rosenberg et al., *Adv. Cancer Res.,* 25:323, 1977 and Rosenberg, *Cancer Treat. Rep.,* 68:233, 1984, both incorporated by reference. In particular, interleukin II, also referred to as T-cell growth factor, has been shown to be a useful adjuvant to adoptive immunotherapy, wherein it is used to stimulate killer T-cell development (see, e.g., Rosenberg, *J. Natl. Cancer Inst.,* 75:595, 1985, incorporated herein by reference). Moreover, adoptive therapy utilizing interleukin II has demonstrated applicability in the treatment of a variety of advanced metastatic cancers in humans (Rosenberg et al., *N. Eng. J. Med.,* 313:1485, 1985, incorporated herein by reference).

Accordingly, it is submitted that the MCF of the present invention, or peptides therefrom, can be utilized in an adoptive immunotherapy protocol in a manner similar to interleukin II. In particular, it is believed that the following proposed protocol will serve as a sufficient basis to teach those skilled in the art of adoptive immunotherapy to utilize MCF in this manner.

Monocytes will be harvested by cell separation using, for example, an IBM cell separator using accepted techniques. These cells would then be incubated with approximately 4 units/ml of MCF or MCF-derived peptides overnight followed by slow continuous infusion of the induced cells into the patients. Such therapy could initially be given 2 to 3 times a week. However, because of the long life span of monocytes it could perhaps be given at more infrequent intervals stretched over a much longer period to time to insure that infiltration into the tumor occurs.

3) Gene Therapy

It is envisioned that the molecular cloning of the 29kD MCF protein will open up new avenues of clinical investigation. In particular, it is believed that recombinant MCF may prove to be of use in gene therapy protocols for human treatment. The basis of this treatment would be to enhance human-defence mechanisms by administering human macrophages or monocytes into which had been inserted a functioning MCF gene. Importantly, in such treatment, the "recombinant" monocytes or macrophages would be able to migrate to sites of tumors and interact with both tumor cells and host lymphocytes. This may lead to an expanded role for adoptive immunity in the treatment of cancer and provide a safe and effective method for delivering immunostimulatory cells host sites.

The first step towards such treatment strategies would be the stable transvection of a human monocyte cell line, such as, for example, U937, to generate MCF-expressing recombinant cells. Technology regarding transvection of human monocyte cell lines is established in the art, for example, as used by Mace and colleagues in transvecting U937 cells with a plasmid bearing the IFN$\beta$ gene (Mace et al., *J. Immunol.*, 147(10):3559, 1991, incorporated herein by reference).

Following this, it is envisioned that one would next proceed to transvect human peripheral blood monocytes expanded in vitro. Expression of cytotoxicity by transvected monocytes may be measured using the assays disclosed herein. One would naturally follow standard and controlled techniques throughout these processes. For example, one would minimize the possibility of subsequently inducing monocyte tumors by monitoring the monocytes for 48 hours in the absence of growth factors for evidence of spontaneous growth which may have resulted from insertional mutagenesis.

Prior to any clinical trials, one would of course analyze the effects of such recombinant cells in an animal model. In vivo monocyte tumor cytotoxicity may be monitored by employing a mouse model, such as, for example, the B16 melanoma model. Inbred mice would be inoculated by tail vein with B16 melanoma cells, and monocytes transformed with recombinant MCF or a control gene. The transformed monocytes could be administered simultaneously with, or subsequent to, the tumor cells. The mice would then be sacrificed 14 days later and pulmonary metastases counted under a dissecting microscope. The results should be statistically analyzed using students T test. Due to the use of human cells, it is contemplated that one would wish to employ nude mice in place of the more commonly used c57B1/6.

Following the animal studies, one could proceed to analyze the recombinant MCF-bearing monocytes or macrophages in human gene therapy regimens. As monocytes are able to migrate to sites of tumor infiltration, they should be particularly useful as vehicles for the delivery of recombinant cytokines, such as MCF, to the tumor bed. Patients with melanoma or non-small cell lung cancer who have failed to respond to conventional therapies are considered to be suitable candidates for inclusion in a clinical trial. The various elements of conducting such a trial, including patient treatment and monitoring, will be known to those of skill in the art in light of the present disclosure.

B. Diagnostic Utility

MCF will additionally be of value as a clinical diagnostic aid. For example, the anti-MCF antibodies described herein will provide an ability to determine MCF blood levels, thereby assisting in maintaining therapeutic blood levels and perhaps in the diagnosis of T-cell malignancies which may be accompanied by high serum MCF levels. Moreover, MCF antiserum may be of use in evaluating T-cell function in normal individuals. Similar uses have been described for the so-called melanoma-associated antigen.

The development of antibodies to a particular antigen whether polyclonal or monoclonal, are well known in the art and can readily be achieved by skilled immunologists. This is the case even where the particular molecule is not antigenic in and of itself, through either the attachment of an immunostimulating ligand such as keyhole limpet hemocyanin, or by finding a species wherein the molecule is antigenic.

As demonstrated herein, polyclonal anti-MCF-antibodies can be prepared by immunizing rabbits. A hetero-antisera of this kind can be quantitated by immunodot assay, western blotting, ELISA and various other immunodiagnostic techniques may be performed with such a hetero-antiserum. Monoclonal antibodies may be developed by a number of accepted techniques, for example, as disclosed by U.S. Pat. Nos. 4,172,124 and 4,271,145, both to Koprowski et al., incorporated herein by reference.

For in vitro diagnostic work, for example, in an immunoassay to quantitate serum MCF levels, the MCF antibody will be used most preferably in an ELISA assay which employs the antibody together with an immuno detection reagent capable of detecting quantitatively specific immune complex formation.

However, in general, immunodiagnostic kits would include reagents appropriate for either detecting patient-generated anti-MCF antibodies (e.g. circulating antibodies) or detecting MCF, for example, tumor-generated MCF, in biological fluids or tissues from patients. As used herein, a biological fluid or tissue includes any fluid or tissue obtained from a patient, including, for example, urine, serum, plasma, and biopsy samples. In the case of MCF antibody-detection kits, such kits would include antigenically pure, and preferably titrated, MCF together with an immuno detection reagent. By antigenically pure MCF is meant an MCF preparation which does not substantially cross-react with non-MCF directed antibodies. Sufficient antigenic purification could be achieved through immunopurification by adsorption with normal sera or chromatography over anti-MCF antibodies as is known in the art.

In the case of MCF antigen detection kits, such kits would typically include antigenically pure, preferably titrated, anti-MCF antibody. By antigenically pure is meant antibody which will not substantially cross-react with antigens other than MCF. As with MCF antigen purification, polyclonal antibody purification could be achieved by immuno chromatography. However, a preferred antibody would be a monoclonal antibody.

In either case, immunodetection kits would include an immunodetection reagent for detecting and/or quantifying the occurrence of specific immunoreactions involving MCF. Typically such reagents include, for example, a radioactive or enzyme-linked ligand. Such ligands are typically associated with either the antibody, antigen or a second antigen or antibody. As noted, a preferred immunodetection system are the various systems based on the ELISA assay. For a further description of the ELISA assay and the various immunodetection reagents, please refer to U.S. Pat. Nos. 4,454,233 and 4,446,232, both incorporated herein by reference. It is believed that these patents provide sufficient disclosure to enable the use of antibody to MCF in a clinical immunoassay.

The present invention has been disclosed in terms of specific embodiments which are believed by the inventor to be the best modes for carrying out the invention. However, in light of the disclosure hereby provided, those of skill in the various arts will recognize that modifications can be made without departing from the intended scope of the invention. For example, although the present invention is disclosed in terms of a Sezary cell hybridoma for MCF production, it is clear that other types of T-cells may be employed. Additionally, numerous embodiments are likely possible for isolation of the factor. Moreover, as biological characterization of the factor progresses, it is likely that more refined and simpler assays will be developed for MCF identification. For example, once an antibody to MCF has been developed, such antibody can be used directly to assay for MCF production by the various cell populations. These and all other modifications and embodiments are intended to be within the spirit and scope of the present invention and appended claims.

What is claimed is:

1. A peptide of from 5 to 9 amino acids in length and having at its amino terminus an amino acid sequence in accordance with seq. id. no. 1, 2 or 3.

2. The protein or peptide of claim 1, further defined as having an amino acid sequence as set forth in seq id no:1.

3. The protein or peptide of claim 1, further defined as having an amino acid sequence as set forth in seq id no:2.

4. The protein or peptide of claim 1, further defined as being 5 amino acid residues in length.

5. The protein or peptide of claim 4, further defined as having an amino acid sequence as set forth in seq id no:3.

* * * * *